United States Patent
Al Kobaisi et al.

(10) Patent No.: US 10,905,649 B2
(45) Date of Patent: Feb. 2, 2021

(54) INJECTABLE COMPOSITION FOR DELIVERY OF A BIOLOGICALLY ACTIVE AGENT

(71) Applicant: CAPSULAR TECHNOLOGIES PTY LTD, Notting Hill (AU)

(72) Inventors: Mohammad Al Kobaisi, Balwyn (AU); David E. Mainwaring, Princes Hill (AU)

(73) Assignee: CAPSULAR TECHNOLOGIES PTY LTD, Notting Hill (AU)

( * ) Notice: Subject to any disclaimer, the term of this patent is extended or adjusted under 35 U.S.C. 154(b) by 0 days.

(21) Appl. No.: 16/092,636

(22) PCT Filed: Apr. 11, 2017

(86) PCT No.: PCT/AU2017/050316
§ 371 (c)(1),
(2) Date: Oct. 10, 2018

(87) PCT Pub. No.: WO2017/177265
PCT Pub. Date: Oct. 19, 2017

(65) Prior Publication Data
US 2019/0125661 A1    May 2, 2019

(30) Foreign Application Priority Data

Apr. 12, 2016 (AU) ................................ 2016901365
Sep. 13, 2016 (AU) ................................ 2016903682

(51) Int. Cl.
| | |
|---|---|
| *A61K 9/00* | (2006.01) |
| *A61K 39/00* | (2006.01) |
| *A61K 39/39* | (2006.01) |
| *A61K 9/107* | (2006.01) |
| *A61K 9/16* | (2006.01) |
| *A61K 9/50* | (2006.01) |
| *A61K 38/09* | (2006.01) |
| *A61K 9/14* | (2006.01) |
| *A61K 38/27* | (2006.01) |
| *A61K 47/36* | (2006.01) |

(52) U.S. Cl.
CPC ............ *A61K 9/0019* (2013.01); *A61K 9/107* (2013.01); *A61K 9/1075* (2013.01); *A61K 9/146* (2013.01); *A61K 9/1652* (2013.01); *A61K 9/5036* (2013.01); *A61K 38/09* (2013.01); *A61K 38/27* (2013.01); *A61K 39/0003* (2013.01); *A61K 39/39* (2013.01); *A61K 47/36* (2013.01); *A61K 2039/55566* (2013.01); *A61K 2039/6093* (2013.01)

(58) Field of Classification Search
CPC .... A61K 9/0019; A61K 9/107; A61K 9/1075; A61K 9/146; A61K 9/1652; A61K 9/5036; A61K 38/09; A61K 38/27; A61K 39/0003; A61K 39/39; A61K 47/36; A61K 2039/55566; A61K 2039/6093
See application file for complete search history.

(56) References Cited

U.S. PATENT DOCUMENTS

| | | | |
|---|---|---|---|
| 2009/0270280 A1* | 10/2009 | Zhang ................... | C09K 8/36 507/211 |
| 2014/0242212 A1* | 8/2014 | Sexton .................. | A23G 4/06 426/2 |
| 2014/0271596 A1 | 9/2014 | Kim et al. | |
| 2014/0286872 A1* | 9/2014 | Zhang ............... | A61K 49/0093 424/9.3 |

FOREIGN PATENT DOCUMENTS

| | | |
|---|---|---|
| EP | 2 425 814 B1 | 3/2012 |
| WO | WO-2008/100044 A1 | 8/2008 |
| WO | WO-2011/003155 A1 | 1/2011 |
| WO | WO-2013/119183 A1 | 8/2013 |
| WO | WO-2016/038221 A1 | 3/2016 |

OTHER PUBLICATIONS

Chua et al., "A single dose biodegradable vaccine depot that induces persistently high levels of antibody over a year," Biomaterials 53, (2015) pp. 50-57 (Available online Mar. 2015).
Kim et al., "Polymersomes Containing a Hydrogel Network for High Stability and Contorlled Release," Small (2013) vol. 9, No. 1, pp. 124-131. (Available online Sep. 7, 2012).
Rojas et al., "Controlled release from a nanocarrier entrapped within a microcarrier," Journal of Colloid and Interface Science, (2006), vol. 301, Issue 2, pp. 617-623. (available online Jun. 16, 2006).

* cited by examiner

*Primary Examiner* — Robert A Wax
*Assistant Examiner* — Olga V. Tcherkasskaya
(74) *Attorney, Agent, or Firm* — Foley & Lardner LLP

(57) ABSTRACT

The invention relates to an injectable composition for rapid and sustained delivery of a biologically active agent and to uses of the injectable composition in the treatment or prevention of a condition in a subject. The injectable composition comprises a water-in-oil emulsion having an aqueous phase dispersed in an oil phase. The aqueous phase comprises a plurality of hydrogel particles and an aqueous liquid and a biologically active agent is contained in the hydrogel particles and in the aqueous liquid.

26 Claims, 17 Drawing Sheets

(A)

(B)

INJECTABLE COMPOSITION FOR DELIVERY OF A BIOLOGICALLY ACTIVE AGENT

CROSS-REFERENCE TO RELATED APPLICATIONS

The present application is the U.S. National Stage of International Application PCT/AU2017/050316, filed Apr. 11, 2017, and claims priority to Australian Patent Application Nos. 2016901365, filed Apr. 12, 2016, and 2016903682, filed Sep. 13, 2016.

TECHNICAL FIELD

The present invention relates to an injectable composition for delivery of a biologically active agent. In particular, the present invention relates to an injectable composition comprising multiple phases for rapid and sustained delivery of a biologically active agent. The invention also relates to uses of the injectable composition in the treatment or prevention of a condition.

BACKGROUND

Biologically active agents may be incorporated in a number of different dosage forms for administration by a number of different routes. These dosage forms may be for example, tablets, capsules, sprays, ointments or patches for delivery of the active agent by routes such as oral, transmucosal or transdermal routes. However, for a variety of reasons, many biologically active agents may not be effectively delivered using routes such as the oral, transmucosal or transdermal routes. This may be because the biologically active agent is susceptible to degradation by enzymes or stomach acid, or is insufficiently absorbed into the systemic circulation due to molecular size and/or charge.

As such, a number of biologically active agents are most suitably administrated by injection. Administration by injection allows an active agent to rapidly enter the systemic circulation and to by-pass the digestive system and first-pass metabolism by the liver. However, repeated injections of an active agent over a period of time may be necessary in order to achieve or maintain a desired effect in vivo. For example, immunisation may require multiple vaccinations, boosters and high doses of vaccine generally to be administered, which can result in increased cost to both industry and the end-users.

Sustained release compositions are of interest in biomedical applications where maintenance of a systemic level of an active agent over a period of time is desired. For injected biologically active agents, sustained release compositions can help to reduce the frequency of injection and increase the duration of action of the active agent or reduce adverse side effects.

A number of injectable sustained release compositions have been described. For example, one form of injectable sustained release composition utilises small diameter polymer particles for the delivery of an encapsulated drug. Such polymer particles are often formed from synthetic degradable polymers such as poly(lactic acid), poly(glycolic acid) or poly(lactic-co-glycolic acid), which breakdown in a biological environment, leading to release of the encapsulated drug over an extended period of time. Drug release may therefore be reliant on the rate of breakdown of the polymer, which may not always give a desired kinetic profile.

There remains a need to develop an injectable composition that can provide a desired release profile for a biologically active agent.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

The present invention provides an injectable composition comprising a biologically active agent that is formulated to provide for initial rapid release of the biologically active agent, followed by sustained delivery of the biological active agent, to a subject in vivo.

In one aspect, the present invention provides an injectable composition for rapid and sustained delivery of a biologically active agent comprising:

a water-in-oil emulsion having an aqueous phase dispersed in an oil phase, the aqueous phase comprising a plurality of hydrogel particles and an aqueous liquid; and a biologically active agent in the hydrogel particles and in the aqueous liquid of the aqueous phase, wherein when administered, the injectable composition provides rapid and sustained delivery of the biologically active agent in vivo.

In some embodiments, the injectable composition of the invention may further comprise an adjuvant. The adjuvant may be present in the oil phase or the aqueous phase of the water-in-oil emulsion of the injectable composition. In one embodiment, the adjuvant is present in the oil phase. The adjuvant may be an adjuvanting oil forming the oil phase of the emulsion.

The hydrogel particles of the aqueous phase of the water-in-oil emulsion comprise a biocompatible material. In one embodiment, the hydrogel particles comprise a crosslinked polysaccharide.

Crosslinked polysaccharide in the hydrogel particles preferably comprises a polysaccharide and a crosslinking agent. In one embodiment, the crosslinking agent comprises functional groups that participate in non-covalent bonding interactions with the polysaccharide.

In one set of embodiments, the crosslinked polysaccharide in the hydrogel particles may comprise a glycosaminoglycan (GAG).

The polysaccharide present in the hydrogel particles may be selected from the group consisting of chitosan, alginate, hyaluronic acid, cellulose, chondroitin sulphate, dermatan sulphate, keratan sulphate, heparin and derivatives thereof. The hydrogel particles may comprise a mixture of two or more such polysaccharides and/or derivatives thereof.

In one embodiment, the crosslinked polysaccharide in the hydrogel particles comprises a polysaccharide selected from the group consisting of chitosan, alginate, chondroitin sulphate, and mixtures thereof.

Chitosan in the hydrogel particles may be crosslinked with a phosphate compound, preferably a tripolyphosphate (TPP) such as sodium tripolyphosphate.

Alginate and chondroitin sulphate in the hydrogel particles may each be crosslinked with a divalent cation derived from an alkaline earth metal. In some particular embodiments, alginate and chondroitin sulphate in the hydrogel particles are crosslinked with calcium ($Ca^{2+}$) or magnesium ($Mg^{2+}$) cations.

The hydrogel particles present in the injectable composition have an average diameter in the range of from about 10 nm to 20 µm, preferably in the range of from about 50 nm to about 5 µm.

In one embodiment, the hydrogel particles further comprise an aqueous insoluble alkaline earth metal phosphate. Preferably, the aqueous insoluble alkaline earth metal phosphate is hydroxyapatite.

In some embodiments, the injectable composition comprises one or more coated hydrogel particles.

In some embodiments, the water-in-oil emulsion of the injectable composition comprises a surfactant. The surfactant can help to facilitate formation of a stable emulsion composition. In one preference, the injectable composition comprises a non-ionic surfactant.

The injectable composition is useful for the delivery of a biologically active agent and may comprise a range of biologically active agents. In accordance with the invention, the biologically active agent is present in the aqueous phase of the water-in-oil emulsion. In particular, the biologically active agent is in the hydrogel particles and in the aqueous liquid of the aqueous phase.

In one embodiment, the biologically active agent is selected from the group consisting of a hormone, an antimicrobial, a therapeutic antibody, a cytokine, a fusion protein, a virus, a bacteria or bacteria fragment, a vaccine and an antigen. In a particular embodiment the biologically active agent is one or more selected from vaccine antigens and hormones. The injectable composition comprises at least one, and may comprise more than one, biologically active agent belonging to one or more of these classes.

In one set of embodiments, the biologically active agent is an antigen. In particular embodiments, the antigen may be Bm86 or TSOL18.

In another set of embodiments, the biologically active agent is a hormone. In particular embodiments, the hormone may be somatotropin or luteinising hormone-releasing hormone (LHRH).

In one form of the injectable composition of embodiments described herein the biologically active agent in the hydrogel particles is conjugated to the particles.

The present invention also provides a method of delivering a biologically active agent to a subject, the method comprising the step of administering an injectable composition of any one of the embodiments described herein to the subject by injection. In particular, the injectable composition of the invention provides rapid delivery of an initial primary dose of the biologically active agent followed by longer term sustained delivery of the active agent to a subject, in vivo.

The present invention further provides a method of treating or preventing a disease or disorder in a subject comprising the step of administering an injectable composition of any one of the embodiments described herein to the subject by injection.

In one embodiment, the injectable composition may be suitably used for the treatment or prevention of a microorganism infection.

In another embodiment, the injectable composition may be suitably used for the treatment or prevention of a viral infection.

In another aspect the present invention provides a process for preparing an injectable composition of embodiments described herein for rapid and sustained delivery of a biologically active agent, the process comprising the steps of:

providing a first aqueous composition comprising a first hydrogel forming component and a second aqueous composition comprising a second hydrogel forming component, at least one of the first aqueous composition and the second aqueous composition comprising a biologically active agent;

combining the first aqueous composition with a lipophilic composition comprising an oil to form an emulsified composition; and combining the second aqueous composition with the emulsified composition under conditions allowing the first hydrogel forming component to react with the second hydrogel forming component to form a plurality of hydrogel particles in situ and thereby provide an injectable composition comprising a water-in-oil emulsion comprising an aqueous phase dispersed in an oil phase, the aqueous phase comprising a plurality of hydrogel particles and an aqueous liquid, and wherein the biologically active agent is contained in the hydrogel particles and in the aqueous liquid of the aqueous phase of the water-in-oil emulsion.

Further aspects appear below in the detailed description.

BRIEF DESCRIPTION OF THE FIGURES

Embodiments of the invention will now be described with reference to the following non-limiting figures in which:

FIG. 1 is a schematic representation showing an injectable composition comprising an antigen in accordance with one embodiment of the invention.

FIG. 2 is a graph showing the antibody titre to Bm86 (ELISA 1:1600 dilution) with a comparative formulation representing a conventional anti-tick composition administered subcutaneously in two injections consisting of primary dose (day 0) and a booster injected after 4 weeks (2×50 μg Bm86/dose), and with an injectable composition of an embodiment of the invention administered subcutaneously as a single injection.

FIG. 3 are graphs showing the amount of Bm86 released over time from a model bulk chitosan hydrogel, with release expressed as (A) the amount of Bm86 detected in the aqueous phase, including the syneresis liquid, and (B) a percentage of the initial Bm86 loading in the composition.

FIG. 4 is a graph showing the release of Bm86 over an 8 week period from samples of model bulk crosslinked chitosan hydrogel with different crosslinking (TTP) densities. Column labels are "S" for the initial syneresis release after 24 hours, with the numbers representing the week number after composition formation, and total amount of Bm86 released over the cumulative 8 week period shown as a percentage.

FIG. 5 illustrates graphs showing the syneresis release of cytochrome c, albumin, myoglobin and pST from samples of model bulk crosslinked chitosan hydrogels at various loading levels expressed as concentration in the syneresis liquid (A-D) and percentage of the initial loading (E), and the relationship between the syneresis release and the isoelectric point of the loaded protein (F).

FIG. 6 shows images of (A) an emulsion composition prior to the in situ formation of hydrogel particles, (B) an injectable composition of an embodiment of the invention with hydrogel particles in situ, and (C) the injectable composition of (B) after storage at 4° C. for 5 months.

Figure 12:
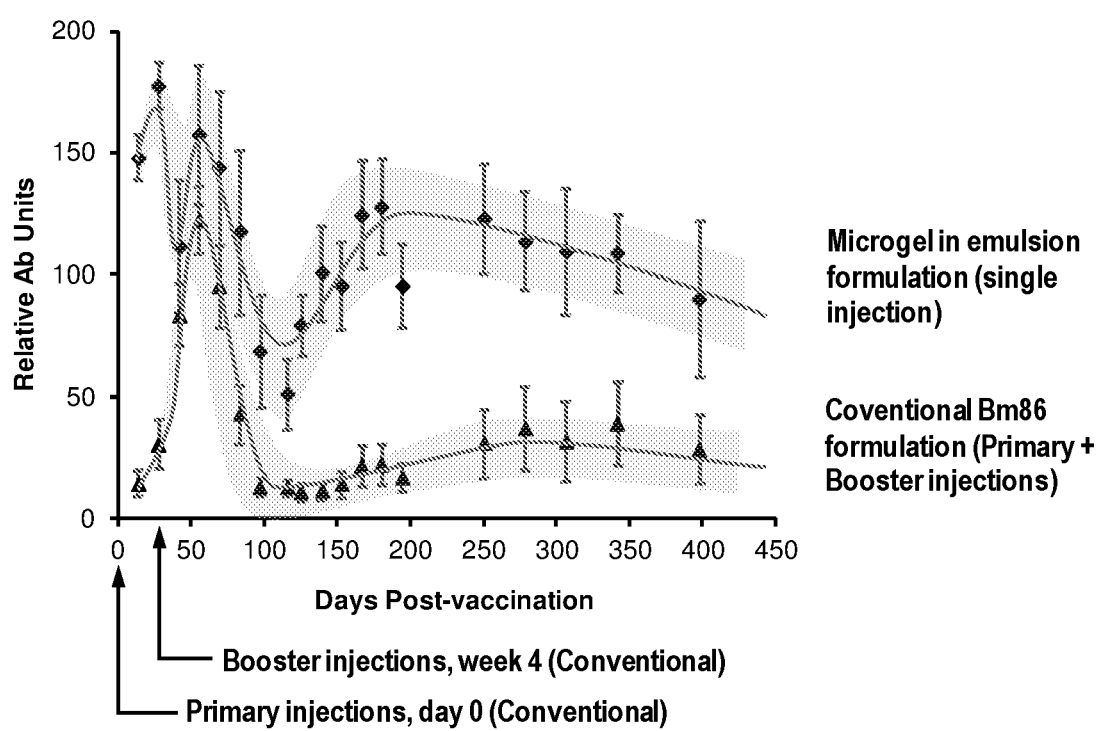

FIG. 12 is a graph showing the immune response in sheep over a period of 400 days exhibited by a comparative formulation comprising Bm86 representing a conventional anti-tick composition administered subcutaneously in two injections consisting of primary dose (day 0) and a booster injected after 4 weeks (2×50 µg Bm86/dose), and by an injectable composition of one embodiment administered subcutaneously as a single injection.

Figure 13:
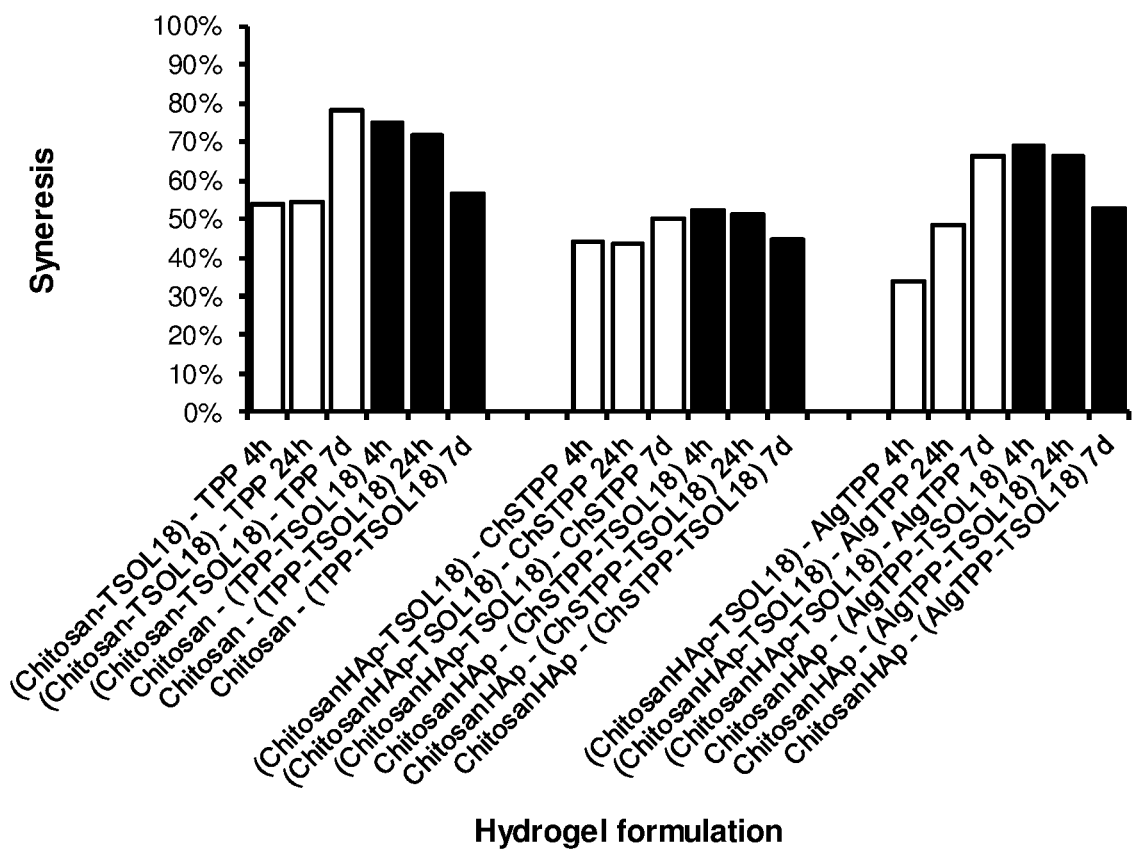

FIG. 13 is a graph illustrating syneresis release of TSOL18 from various model uncoated and coated chitosan based hydrogels over 1 week.

Figure 14:
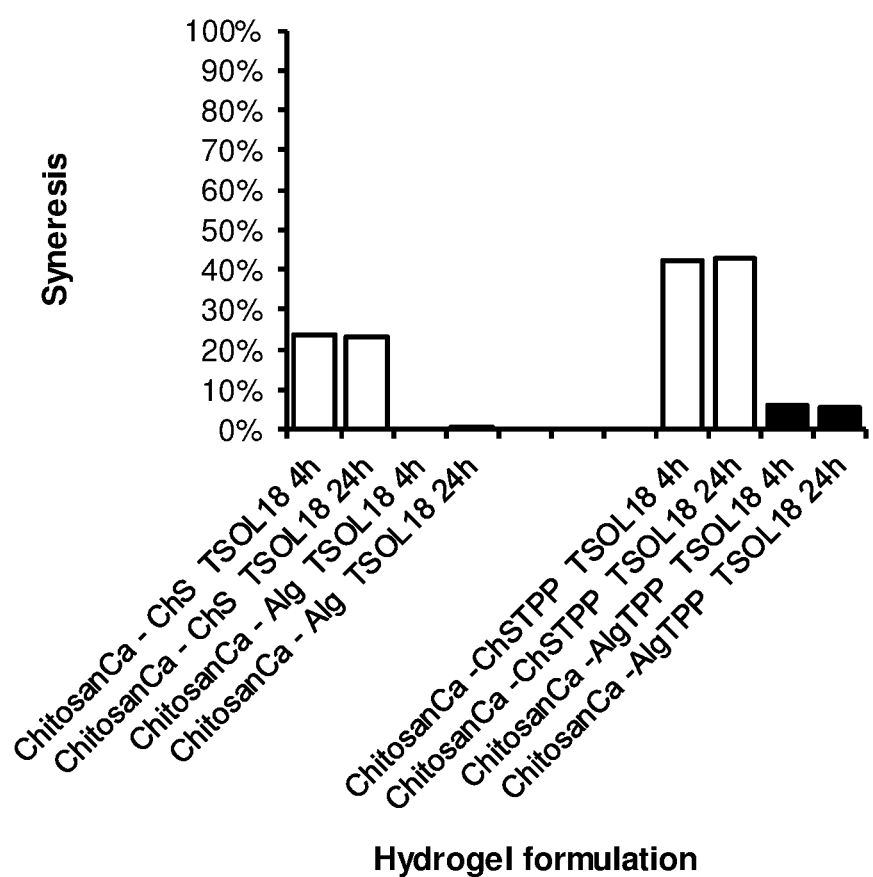

FIG. 14 is a graph illustrating syneresis release of TSOL18 from various model crosslinked and non-crosslinked chitosan hydrogels coated with a crosslinked alginate or chondroitin sulphate coating over 1 day.

Figure 15:
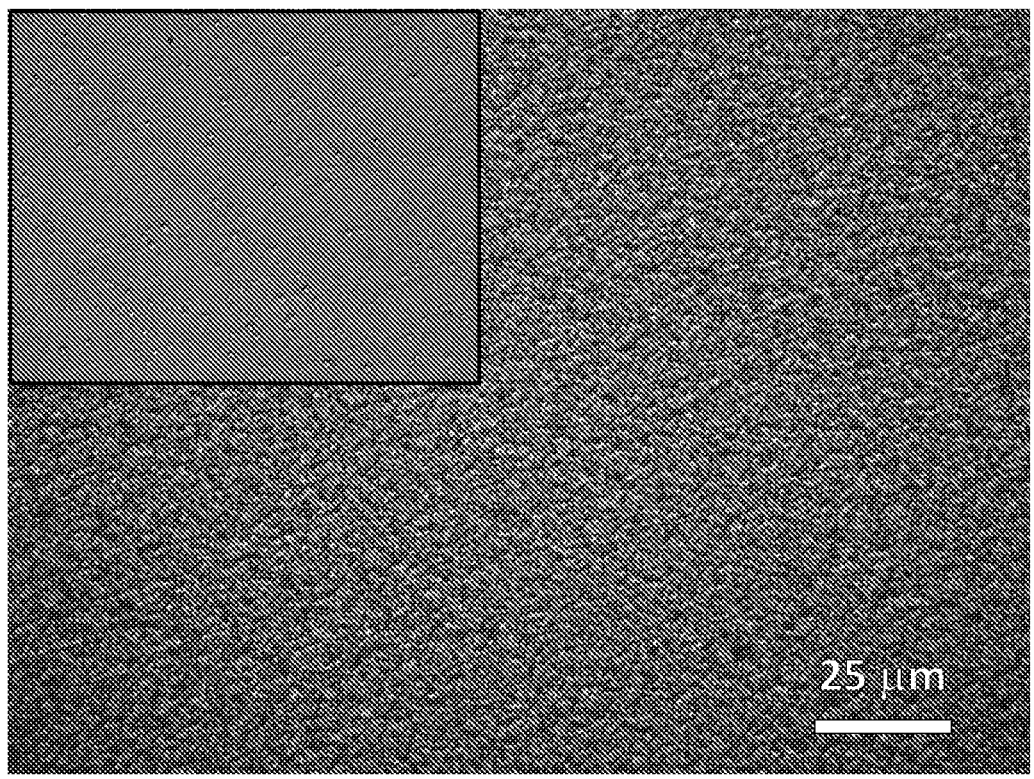

FIG. 15 shows a micrograph of an injectable composition containing TSOL18 in accordance with an embodiment of the invention, with a 1:10 dilution of the composition (in inset) showing particles of microhydrogel in the emulsion.

Figure 16:
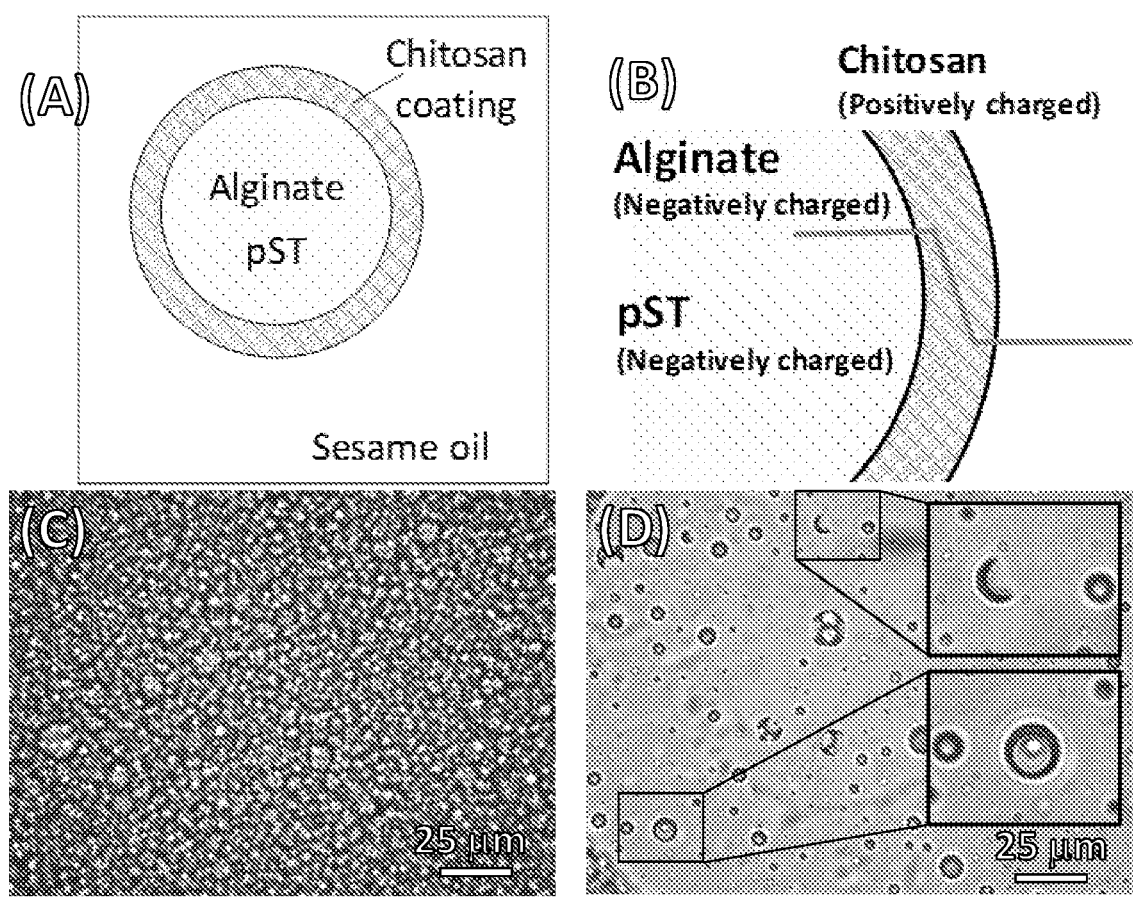

FIG. 16 shows (A) a schematic representation of a porcine somatotropin (pST) loaded alginate hydrogel particle bearing a chitosan coating, (B) a schematic representation of the barrier effect of the coating on the release of (pST), (C) light microscope micrograph of an injectable composition comprising alginate hydrogel coated with chitosan in accordance with one embodiment of the invention, and (D) the sample shown in (C) diluted 1:10 in sesame oil selectively showing partially formed and broken chitosan shells.

Figure 17:
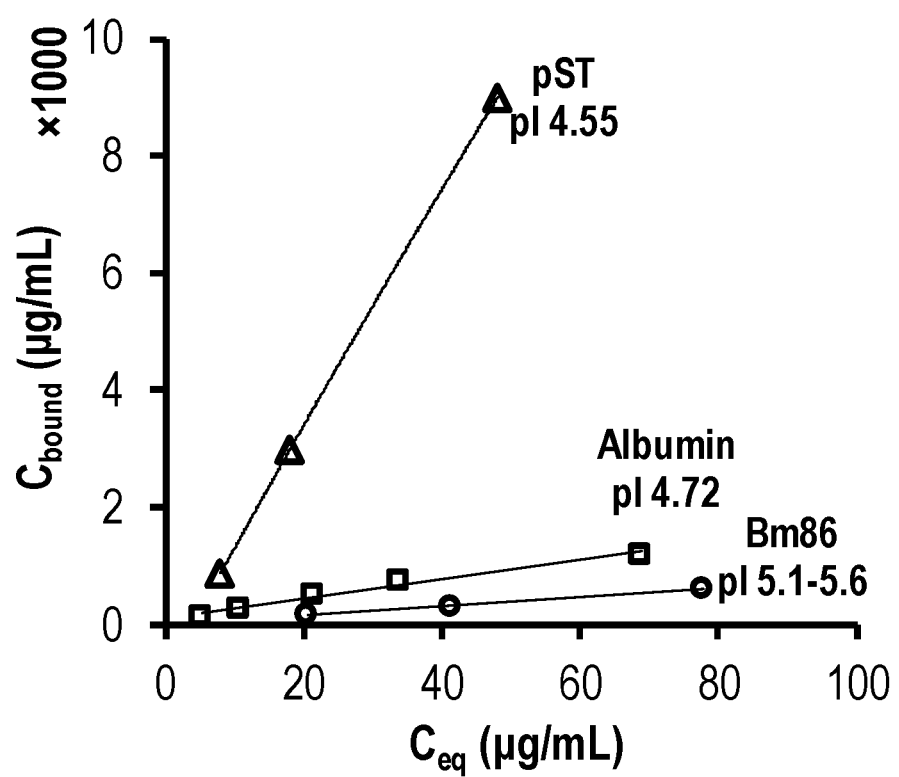

FIG. 17 is a graph illustrating the initial fractionation (protein partition) of porcine somatotropin (pST), albumin and Bm86 after hydrogel formation and the completion of syneresis process, where electrostatic binding of pST, Bm86 and albumin with a model bulk chitosan—HAp hydrogel formed with 0.08 M TPP in 1% ChS crosslinking is measured at equilibrium.

DETAILED DESCRIPTION OF THE INVENTION

The present invention is based on the finding that both rapid and sustained delivery of a biologically active agent in vivo is able to be achieved through the use of an injectable composition as described herein.

The injectable composition of the invention is able to deliver an initial primary dose of the biologically active agent, followed by more sustained delivery of the active agent over a period of time, which reduces the need for repeated injections.

In one aspect the present invention provides an injectable composition for rapid and sustained delivery of a biologically active agent comprising:

a water-in-oil emulsion having an aqueous phase dispersed in an oil phase, the aqueous phase comprising a plurality of hydrogel particles and an aqueous liquid; and a biologically active agent in the hydrogel particles and in the aqueous liquid of the aqueous phase, wherein when administered, the injectable composition provides rapid and sustained delivery of the biologically active agent in vivo.

In the context of the present invention, "rapid" delivery relates to delivery of the biologically active agent immediately upon administration of the injectable composition to a subject, or shortly thereafter. The rapid delivery provides for an initial dose of the biologically active agent immediately or shortly after injection of the composition of the invention to elicit an initial therapeutic effect.

"Sustained" delivery relates to delivery of the biologically active agent subsequent to the initial rapid delivery. Sustained delivery thus occurs over a time period that is substantially longer than rapid delivery. The sustained delivery provides for a dose of the biologically active agent over a longer term and therefore prolongs the therapeutic effect provided by the active agent. In some embodiments, sustained delivery may be for a time period of at least 24 hours. In particular embodiments, sustained delivery may be for time period of at least several days or weeks, or even months.

It is believed that the ability of the injectable composition to provide for rapid and sustained delivery of a biologically active agent is assisted by the composition comprising multiple phases. The desired in vivo delivery profile of the biologically active agent is thus influenced by the different phases in the composition.

In particular embodiments, the injectable composition of the invention comprises at least three phases. In some embodiments, the injectable composition may comprise more than three phases, such as four, five, six or more phases, in total. The injectable composition of the invention may be regarded as a multiphasic composition.

In one embodiment, the injectable composition of the invention is triphasic.

The injectable composition of the invention comprises a water-in-oil emulsion. A skilled person would understand that a water-in-oil emulsion comprises an oil phase and an aqueous phase dispersed in the oil phase. The oil phase forms the continuous phase of the emulsion while the aqueous phase forms the dispersed phase.

The aqueous phase of the water-in-oil emulsion comprises an aqueous liquid. The aqueous phase also comprises a plurality of hydrogel particles, which are dispersed in the aqueous liquid. Thus the aqueous liquid and the hydrogel particles each form part of the aqueous phase of the water-in-oil emulsion.

In some embodiments, the injectable composition of the invention comprises at least three phases and these may be a first phase, a second phase and a third phase. The first phase may be provided by the oil phase of the water-in-oil emulsion. At least two further phases may be provided by the aqueous phase of the water-in-oil emulsion. In particular, the aqueous liquid and the hydrogel particles of the aqueous phase of the emulsion may provide a second phase and a third phase of the injectable composition, respectively.

The oil phase of the water-in-oil emulsion comprises at least one physiologically acceptable oil and may comprise a mixture of such oils. Physiologically acceptable oils are generally hydrophobic and liquid at a temperature between 20° C. and 40° C.

A range of suitable physiologically acceptable oils may be used in the injectable composition of the invention.

In some embodiments, the oil phase may comprise one or more oils selected from the group consisting of fatty acids; fatty acid esters; esters of polyethylene glycols, for example mono- and di-esters; hydrocarbon oils, for example natural hydrocarbon oils; and steroids, for example cholesterol.

In one embodiment, the oil phase may comprise one or more oils selected from fatty acids; fatty acid esters; esters of polyethylene glycols; and hydrocarbon oils.

Suitable fatty acids and fatty acid esters may be those having an aliphatic saturated or unsaturated chain comprising from 6 to 24 carbon atoms. Unsaturated aliphatic chains may be mono- or poly-unsaturated. Some particular fatty acids may be long chain $C_{12}$-$C_{24}$ fatty acids e.g. $C_{15}$-$C_{22}$ fatty acids, and medium chain $C_6$-$C_{12}$ fatty acids. Among these, include poly-unsaturated fatty acids such as omega-3 oils, for example, eicosapentanoic acid (EPA), docosohexaenoic acid (DHA), alpha-linoleic acid (ALA). Combinations of such compounds are also contemplated. Fatty acid esters may be triglycerides, as well as esters of glycerol (particularly tri-esters) with a combination of fatty acids and lower molecular weight acids e.g. succinic acid (fatty acid triglycerides are a particular example of glycerides). Oils containing triglycerides may also contain mono- and/or di-glycerides, e.g. as a minor part of the glyceride content (less than 50 mol %).

In some embodiments, the oil phase may comprise a mixture of oils, for example fatty acid macrogolglycerides, also known as polyoxylglycerides, which are mixtures of fatty acid monoesters, diesters and triesters of glycerol and fatty acid monoesters and diesters of polyethylene glycol; examples are oleoyl macrogolglycerides and linoeoyl macrogolglycerides.

Suitable hydrocarbon oils may be mineral oils or terpenes.

Particular terpenes may be triterpenes such as, for example, squalene.

Particular mineral oils may comprise a mixture of several hydrocarbon chains of different lengths, including small chains (≤C14) and longer chain (>C14) hydrocarbon lengths. Examples of mineral oils of a pharmaceutical grade include light liquid paraffin and light mineral oil.

Alternative or additional oils, which may be included in the oil phase in combination with or in place of the above oils include plant or vegetable oils, such as peanut oil, safflower oil, sunflower oil, soya bean oil, cottonseed oil, chaulmoogra oil, corn oil, jojoba oil, pesic oil, olive oil, sesame oil, almond oil, castor oil, canola oil, linseed oil, squalene and coconut oil; fish oils such as shark oil, orange roughy oil, Menhaden oil and cod liver oil; animal oils such as mink oil, lard oil and chicken fat oil; and synthetic oils such as ethyl oleate.

In some embodiments, the oil phase may comprise a physiologically acceptable oil having adjuvanting properties. The physiologically acceptable oil is therefore an adjuvant and may be referred to as an adjuvanting oil.

In other embodiments, the oil phase may comprise a non-adjuvanting physiologically acceptable oil (i.e. a passive oil). In such embodiments, the oil does not possess adjuvanting properties. The passive oil may be regarded as being chemically inert. However, if desired, an adjuvant may be contained in the passive oil. Such adjuvants are preferably oleophilic or oil soluble and may be dissolved or suspended in the oil.

The oil phase is derived from oils used to prepare the injectable composition of the invention. The oil phase may be derived from commercially available preparations containing combinations of oils, optionally with other components. For example, commercially available emulsion preparations comprising a physiologically acceptable oil may be used to produce the oil phase of the injectable composition. Such commercial emulsion preparations may desirably contain one or more emulsifiers, in which case the emulsifier may also be present in the composition of the invention. Examples of commercial preparations of oil adjuvants include the series of adjuvants sold by SEPPIC under the trademark MONTANIDE™. A particular example is sold by SEPPIC under the trademark MONTANIDE™ ISA 61, which comprises a light mineral oil and an emulsifier comprising mannitol and oleic acid. Other commercial formulations such as those sold under the trademark FLUAD® (Novartis) and under the trademark PANDEMRIX®(GSK), which contain MF59 and AS03 oil adjuvants, may also be used to form the oil phase.

The water-in-oil emulsion of the injectable composition also comprises an aqueous phase. In accordance with the requirements of the invention, the aqueous phase comprises a plurality of hydrogel particles and an aqueous liquid.

A skilled person would understand that the term "hydrogel particles" refers to discrete colloidal portions of hydrogel material. Hydrogel materials are polymer matrices in a gel state that are swollen or hydrated by an aqueous liquid.

The hydrogel particles of the injectable composition described herein will generally be low modulus, soft materials comprising a low solids content and high water content. In some embodiments, the hydrogel particles may have a Young's modulus in the range of from about 5 kPa to 700 kPa. The hydrogel particles may further have a water content of at least 60%.

In some embodiments, the hydrogel particles may be microhydrogels. The term "microhydrogels" is used herein as a reference to discrete portions of hydrogel having at least one dimension in the nanometer (nm) to micrometer (μm) range. Such microhydrogels may be nanometer or micrometer sized droplets comprising or composed of hydrated polymer gel.

The hydrogel particles are dispersed in and may be surrounded by the aqueous liquid.

Generally, the aqueous liquid comprises water.

It is contemplated that other compounds or components may be present in the aqueous liquid if desired. For example, in some embodiments the aqueous liquid may comprise an adjuvant, which can be dissolved or suspended in the liquid. When used, such adjuvants are generally hydrophilic adjuvants.

The hydrogel particles of the aqueous phase are biocompatible and are formed from biocompatible materials. Biocompatibility is a concept known to those in the art. Biocompatible substances are those that elicit acceptable immune responses. Accordingly, as used herein the term "biocompatible" refers to a substance or component that is biologically compatible such that it substantially does not elicit an adverse immune, toxic or injurious response in vivo, or adversely integrates with a particular cell type or tissue.

The hydrogel particles can be colloidal portions of hydrogel material having a diameter in the range of from about 10 nm to 20 µm, preferably from about 50 nm to about 5 µm. Hydrogel particles according to such embodiments may be referred to herein as microhydrogels. Hydrogel particle diameter may be controlled by the choice of the oil phase and the choice of any surfactant or emulsifier used to prepare the injectable composition. Hydrogel particle diameter may be ascertained using a range of optical techniques, such as dynamic light scattering, light microscopy and confocal laser scanning microscopy.

The hydrogels particles preferably comprise or are composed of a crosslinked polymer. In addition to being biocompatible, the crosslinked polymer is hydrophilic and amenable to aqueous solvation.

A range of crosslinked polymers may be suitable for the hydrogel particles. Polymers in the hydrogel may be chemically or physically crosslinked.

Crosslinked polymers suitable for the hydrogel particles may be produced when a first component and a second component react or interact to form a three-dimensional macromolecular network structure that is held together via intermolecular bonds. The macromolecular network can be regarded as a polymer matrix.

The first component may be a polymer component, while the second component may be a crosslinking component. The crosslinking component may be provided by a crosslinking agent. The crosslinking agent may be a small molecule or a macromolecule, such as a further polymer.

Crosslinking between the polymer component and the crosslinking component may occur via physical, covalent or non-covalent bonds.

Crosslinked polymers suitable for the hydrogel particles may comprise or be formed from polymers and crosslinking agents of natural or synthetic origin.

In one set of embodiments, the hydrogel particles in emulsion may be formed with a neutral polymer, which is crosslinked via physical, covalent or non-covalent bonds. A neutral polymer may be one that has no ionisable functional groups. Consequently, hydrogel particles formed with a neutral polymer may carry no net charge at physiological pH.

In one set of embodiments, the hydrogel particles may be formed with a charged polymer, which is crosslinked via non-covalent bonds. The charged polymer may be a polyelectrolyte. The charged polymer may be selected from a cationic polymer, an anionic polymer, a zwitterionic polymer, or a combination thereof.

Hydrogel particles formed with a charged polymer may comprise groups that are ionisable, such that the hydrogel particles carry a net charge at physiological pH. Charged hydrogel particles can influence both the uptake and release of a biologically active agent through electrostatic interactions, as well as the kinetics of release. Hydrogel particles formed with a charged polymer may therefore affect both the initial release of the biologically active agent as well as its longer term sustained release.

In one embodiment, the hydrogel particles comprise a crosslinked biopolymer. Biopolymers may be polymeric molecules obtained from, or derived from, natural sources.

In one embodiment, the hydrogel particles comprise a crosslinked polysaccharide. The crosslinked polysaccharide is formed when at least one polysaccharide is combined with at least one crosslinking agent.

In one embodiment, the crosslinked polysaccharide may comprise a glycosaminoglycan (GAG). Glycoaminoglycans are unbranched polysaccharides based on a repeating disaccharide unit. The disaccharide unit can consist of an amino sugar (N-acetylglucosamine or N-acetylgalactosamine) and either a uronic sugar (glucuronic acid or iduronic acid) or galactose. GAGs may also be esterified by sulphur containing groups. Some examples of glycosaminoglycans are chondroitin sulphate, dermatan sulphate, keratan sulphate, and heparin. In one preference, the hydrogel particles comprise a crosslinked glycosaminoglycan.

Hydrogel particles comprising a crosslinked polysaccharide may comprise a polysaccharide selected from the group consisting of chitosan, alginate, hyaluronic acid, cellulose, chondroitin sulphate, dermatan sulphate, keratan sulphate, and heparin, as well as salts thereof and derivatives thereof. Polysaccharides such as chitosan, alginate, hyaluronic acid, chondroitin sulphate and cellulose may possess adjuvanting properties, and can assist in modulating the release of the biologically active agent from the injectable composition in vivo.

Crosslinked polysaccharide in the hydrogel particles may be charged (i.e. carry a net positive or negative charge) or uncharged.

In one preference, the crosslinked polysaccharide comprises a polysaccharide selected from chondroitin sulphate, alginate and chitosan, a salt thereof or a derivative thereof.

Derivatives of chitosan may be chitosan-dextran sulphate, N-trimethyl chitosan, N-carboxymethyl chitosan, and lipo- and glycoconjugated derivatives of oligochitosans.

Polysaccharides are combined with crosslinking agents to form a three-dimensional crosslinked macromolecule. It would be appreciated that the polysaccharide and the crosslinking agent must be capable of interacting with one another in order to form the crosslinked polymer. Accordingly, the polysaccharide and the crosslinking agent may each comprise a chemical moiety bearing a functionality that is capable of crosslinking.

Suitable crosslinking agents may comprise or be composed of a chemical moiety that is capable of interacting with a functional group present on the polysaccharide via covalent or non-covalent bonding mechanisms. In some embodiments, the chemical moiety may bear functional groups that are capable of interacting with functional groups present on the polysaccharide via covalent or non-covalent bonding mechanisms.

In one form, suitable crosslinking agents may be capable of participating in non-covalent bonding interactions with the polysaccharide. The crosslinking agents may comprise functional groups that can participate in such non-covalent bonding interactions.

The polysaccharide may comprise an ionisable functional group (such as an amino, carboxylic acid or sulphonate group), that is capable of forming a cationic or anionic functional group, and the crosslinking agent may comprise a complementary ionisable functionality that is capable of bonding with one or more functional groups of the polysaccharide through non-covalent interactions. Thus the resulting crosslinked polysaccharide may be crosslinked via electrostatic or ionic bonds.

Ionisable functional groups in the polysaccharide may impart a net charge to the crosslinked polysaccharide if some of the ionisable functionalities remain free and not bound with a complementary crosslinking agent. These free ionisable functional groups may be available to interact with an oppositely charged biologically active agent contained in the hydrogel particles via non-covalent interactions such as electrostatic interactions. This could aid in the retention of the active agent in the hydrogel particles and thus influence the delivery profile of the biologically active agent over the time period where sustained release is desired.

In one embodiment, the hydrogel particles comprise crosslinked chitosan.

Chitosan is a linear polyaminosaccharide composed of randomly distributed β-(1-4)-linked D-glucosamine (a deacetylated unit) and N-acetyl-D-glucosamine (an acetylated unit). The degree of deacetylation (% DA) can be determined by NMR spectroscopy, and the % DA in commercial chitosan is in the range 60-100%.

Chitosan is biocompatible, enzymatically biodegradable (for example by lysozyme hydrolysis), and non-toxic (its degradation products are relatively non-immunogenic and non-carcinogenic).

The amino group in chitosan has a pKa value of approximately 6.5. Thus, chitosan is positively charged (i.e. the amino groups are protonated) and soluble in acidic to neutral solution with a charge density dependent on pH and the % DA-value. In other words, chitosan can act as a positively charged polyelectrolyte under physiological conditions and thus has appropriate functionality to be crosslinked with a crosslinking agent.

Chitosan suitable for use in the hydrogel particles may be of a range of molecular weights. In an embodiment, the chitosan is a low molecular weight chitosan having a molecular weight (Mw) of between 40-250 kDa. In some embodiments, the Mw is preferably in the range of 50-200 kDa and even more preferably 100-180 kDa.

Chitosan may be crosslinked by a range of crosslinking agents or compounds. Suitable crosslinking agents or compounds may comprise anionic functionalities. The anionic groups are capable of interacting with positively charged amino groups in chitosan to produce a crosslinked chitosan that is held together via non-covalent electrostatic bonds.

In one form, the hydrogel particles may comprise chitosan crosslinked with a phosphate compound. The phosphate compound can be selected from those suitably functionalised as to promote intermolecular crosslinking between chains of chitosan. The phosphate compound may be suitably chosen to facilitate rapid (spontaneous) crosslinking and thus hydrogel formation when combined with the chitosan. Suitable crosslinking phosphate compounds include tripolyphosphate, and salts thereof. Commonly known salts of tripolyphosphate include sodium tripolyphosphate and potassium tripolyphosphate. Sodium tripolyphosphate (STPP, sometimes STP or sodium triphosphate or TPP), with formula $Na_5P_3O_{10}$, is a polyphosphate of sodium. It is the sodium salt of triphosphoric acid. In one preference, the crosslinking agent is TPP.

In some embodiments, chitosan may be crosslinked by compounds comprising electrophilic functional groups. A skilled person would appreciate that the electrophilic group may react with nucleophilic amino groups in the chitosan, resulting in the formation of a covalent carbon-carbon bond between the polyaminosaccharide and the crosslinking agent. Suitable crosslinking agents may comprise electrophilic groups selected from ketone, aldehyde and epoxide functional groups. In one preference, the crosslinking compound may be selected from glutaraldehyde and epichlorohydrin.

Crosslinked chitosan useful for the hydrogel particles may comprise chitosan and a crosslinking agent in a suitable molar ratio. In some embodiments, it may be desirable to vary the level of crosslinking by adjusting the molar ratio of chitosan to crosslinking agent. Variation in the crosslink density may be used to modify the physical properties of the hydrogel particles and/or to modulate the release of a bioactive agent from the hydrogel particles.

In some embodiments, the molar ratio of chitosan to crosslinking to chitosan agent is from about 12:1 to about 50:1, preferably from about 25:1 to about 2040:1, more preferably from about 37:1 to about 1030:1.

In some embodiments, it may be preferable for the crosslinked chitosan to comprise a relatively low crosslinking ratio (i.e. a low molar concentration of crosslinking agent) as this may result in ionised groups in the chitosan remaining charged and thus available to participate in non-covalent interactions with a biologically active agent contained in the hydrogel particles.

In other embodiments, it may be preferable for the crosslinked chitosan to comprise a relatively high crosslinking ratio (i.e. excess crosslinking agent relative to polysaccharide). A high crosslink density may in some embodiments advantageously assist with rapid polymer network and hydrogel formation as well as help to improve the mechanical properties of the hydrogel particles and/or help produce more uniform morphology.

In one embodiment, the hydrogel particles comprise crosslinked alginate.

Alginate is naturally occurring polysaccharide that is isolated from seaweed and is composed of a block copolymer comprising covalently linked blocks comprising (1-4)-linked β-D-mannuronate (M) and α-L-guluronate (G) residues. The proportion and distribution of M and G may determine the physical and chemical properties of the alginate.

Alginate has biocompatibility and low toxicity and can undergo crosslinking and gelation under mild conditions. At neutral pH (approximately pH 7), alginate may be anionic and carry a net negative charge.

Alginate suitable for use in the hydrogel particles may be of a range of molecular weights. In some embodiments, alginate may have a molecular weight in the range of from about 40 to 270 kDa. In an embodiment, the alginate may have medium molecular weight, which gives a viscosity of >2000 cP at a concentration of 2% in water at 25° C.

Crosslinking of alginate may be induced by combining the alginate with a positively charged molecule or compound, such as a cation. Alkaline earth metal compounds may provide a source of divalent cations and thus such compounds may be used as crosslinking agents to crosslink the alginate. Alkaline earth metal compounds useful as crosslinking agents may be calcium or magnesium compounds. In one embodiment the alginate may be crosslinked electrostatically with cations such as calcium ($Ca^{2+}$) or magnesium ($Mg^{2+}$) cations.

In one preference, the hydrogel particles comprise alginate crosslinked with calcium cations. Calcium cations may participate in selective ionic bonding with guluronate residues in alginate chains to induce gel formation and crosslinking via non-covalent bonding interactions.

Calcium cations may be provided by a range of calcium compounds as crosslinking agents. Suitable calcium compounds may be selected from calcium chloride ($CaCl_2$), calcium sulphate ($CaSO_4$) and calcium carbonate ($CaCO_3$). In one preference, the calcium compound is calcium chloride.

Crosslinked alginate useful for the hydrogel particles may comprise alginate and a cation (such as a calcium cation) in a suitable molar ratio. In some embodiments, it may be desirable to vary the level of crosslinking by adjusting the ratio of alginate to cation.

For instance, it has been found that stable injectable compositions comprising hydrogel particles in a water-in-oil emulsion can be prepared by combining sesame oil with 2% alginate in water and 5.6% $CaCl_2$ in water at volumetric ratios of 2:1:0.2 to 2:1:1 and 2:0.5:0.2 to 2:0.5:1 (based on oil:alginate solution:$CaCl_2$ solution).

The crosslinking of alginate with a cation also neutralises the negative charge carried by alginate at neutral pH. This neutralisation of negative charge allows hydrogel particles comprising alginate to efficiently contain negatively charged biologically active agents, which might otherwise be difficult to achieve due to the potential for unfavourable electrostatic interactions between the negatively charged biologically active agent and the anionic alginate polymer.

Variations in cation concentration can be used to alter the crosslink density of the alginate containing hydrogel particles and this can be used to modify the physical properties of the hydrogel particles and/or to modulate the release of a bioactive agent from the hydrogel particles. For example, when the concentration of cation is insufficient to neutralise all negatively charged groups in the alginate, the alginate may therefore have residual anionic groups. Hydrogel particles comprising the alginate may thus carry a net negative charge at physiological pH. In some embodiments, this residual net negative charge may advantageously help to modulate the uptake and release of a biologically active agent from the hydrogel particle. For example, in the case of a positively charged biologically active agent, a net negative charge carried by a hydrogel particle may help to inhibit rapid release of the active agent so that more sustained release of the agent can be achieved over a prolonged period of time.

In some embodiments, the hydrogel particles may comprise or be composed of a glycosaminoglycan (GAG). Glycosaminoglycans (GAGs) are long unbranched polysaccharides containing a repeating disaccharide unit. The repeating disaccharide unit contains either of two modified sugar (N-acetylgalactosamine or N-acetylglucosamine), and generally a uronic acid (glucuronate or iduronate). GAGs may also be esterified by sulphur containing groups.

In one set of embodiments, the hydrogel particles may comprise or be composed of at least one glycosaminoglycan (GAG) selected from the group consisting of chondroitin, hyaluronate, keratan, dermatan, heparin, and derivatives thereof, such as chondroitin sulphate, sodium hyaluronate, keratan sulphate, dermatan sulphate, and heparin sulphate.

In one embodiment, the glycosaminoglycan (GAG) is chondroitin sulphate. Chondroitin sulphate is a sulphated glycosaminoglycan composed of an unbranched polysaccharide chain of alternating sugars (N-acetyl-galactosamine and glucuronic acid). The sulphate is covalently attached to the sugar. If some glucuronic acid residues are epimerized into L-iduronic acid, the resulting disaccharide is then referred to as dermatan sulphate. Since the molecule has multiple negative charges at physiological pH (approximately pH 7), a cation is present in salts of chondroitin sulphate. Commercial preparations of chondroitin sulphate typically are the sodium salt.

Chondroitin sulphate is a major component of the extracellular matrix, and is important in maintaining the structural integrity of the tissue. It is also an important structural component of cartilage, as part of aggrecan, and provides much of its resistance to compression through the tightly packed and highly charged sulphate groups of chondroitin sulphate.

A chondroitin chain can have over 100 individual sugars, each of which can be sulphated in variable positions and quantities. Each monosaccharide may be left unsulphated, sulphated once, or sulphated twice. Most commonly, the hydroxyls of the 4 and 6 positions of the N-acetyl-galactosamine are sulphated, with some chains having the 2 position of glucuronic acid sulphated. Sulphation is mediated by specific sulphotransferases. Sulphation in these different positions confers specific biological activities to chondroitin glycosaminoglycan chains.

Some old classification terminology exists as follows: Chondroitin sulphate A—sulphation site is carbon 4 of the N-acetylgalactosamine sugar (also known as chondroitin-4-sulphate); Chondroitin sulphate B—an old name for dermatan sulphate, which is no longer classified as a form of chondroitin sulphate; Chondroitin sulphate C—sulphation site is carbon 6 of the N-acetyl-galactosamine sugar (also known as chondroitin-6-sulphate); Chondroitin sulphate D—sulphation sites are carbon 2 of the glucuronic acid and 6 of the N-acetylgalactosamine sugar (also known as chondroitin-2,6-sulphate); and Chondroitin sulphate E—sulphation sites are carbons 4 and 6 of the N-acetylgalactosamine sugar (also known as chondroitin-4,6-sulphate). All such derivatives are encompassed herein as "chondroitin sulphate" as contemplated for use in the present invention.

Chondroitin sulphate useful for inclusion in the hydrogel particles may have an average molecular weight of from about 5,000 Da to about 150,000 Da, from about 10,000 Da to about 50,000 Da, or from about 10,000 Da to about 40,000 Da. Other molecular weights can however be used.

When the hydrogel particles comprise or are composed of a glycosaminoglycan (GAG) such as chondroitin sulphate, a net charge can be carried by the hydrogel particles at physiological pH and this charge may advantageously assist with modulating the release of a biologically active agent contained in the particles. In particular, chondroitin sulphate may interact with a positively charged biologically active agent to provide higher entrapment and retention of the active agent in the hydrogel particles. Electrostatic interactions between the negatively charged chondroitin sulphate and a positively charged biologically active agent can also help to limit premature release of the active agent or improve the long-term release profile of the active from the hydrogel particle.

Furthermore, chondroitin sulphate may have immunoregulatory effects, and may also interact with polysaccharides such as chitosan via non-covalent bonding interactions to contribute to the crosslinking of the polysaccharide.

In some embodiments, the hydrogel particles may comprise or be composed of a crosslinked glycosaminoglycan.

Sulphated glycosaminoglycans such as chondroitin sulphate may be crosslinked with a suitable crosslinking agent. In one embodiment, the crosslinking agent may be a cation, such as a divalent cation sourced from alkaline earth metal compounds. In one embodiment, the chondroitin sulphate may be crosslinked with cations such as calcium ($Ca^{2+}$) or magnesium ($Mg^{2+}$).

In one embodiment, the hydrogel particles comprise chondroitin sulphate crosslinked with calcium cations. Calcium cations may be provided by a range of calcium compounds as crosslinking agents. Suitable calcium compounds may be selected from calcium chloride ($CaCl_2$), calcium sulphate ($CaSO_4$) and calcium carbonate ($CaCO_3$). In one preference, the calcium compound is calcium chloride.

Crosslinked chondroitin sulphate useful for the hydrogel particles may comprise chondroitin sulphate and a cation (such as a calcium cation) in a suitable molar ratio. In some embodiments, the molar ratio of chondroitin sulphate to cation may be from 4:1 to 1:10.

Similar to alginate discussed above, variations in cation concentration can be used to alter the crosslink density and charge of the crosslinked glycosaminoglycan containing hydrogel particles. For example, when the GAG is sulphated GAG (for example chondroitin sulphate), the concentration of cation may be insufficient to neutralise all negatively charged groups in the GAG and thus the GAG may carry a net negative charge at physiological pH due to residual anionic groups. This residual net negative charge may advantageously help to modulate the uptake, retention and release of a positively charged biologically active agent from the hydrogel particle according to mechanisms discussed above.

In some embodiments, hydrogel particles of the injectable composition of the invention may comprise a mixture of polysaccharides, such as mixture of two different glycosaminoglycans, or a mixture of a glycosaminoglycan and at least one other polysaccharide. At least one of the polysaccharides is crosslinked. In some embodiments, the crosslinked polysaccharide can be crosslinked chitosan, crosslinked alginate or crosslinked chondroitin sulphate, as described herein.

In one form, the hydrogel particles comprise a mixture of oppositely charged polysaccharides. For example, the hydrogel particles may comprise a mixture of chitosan and chondroitin sulphate. In such embodiments, negatively charged sulphate groups on the chondroitin sulphate may interact with positive amino groups present in chitosan via electrostatic interactions to thereby form a crosslinked macromolecule. The crosslinked macromolecule may be considered to be a hybrid crosslinked polysaccharide that is composed of a mixture of chitosan and chondroitin sulphate. The crosslinked macromolecule, which is composed of at least two electrostatically linked polysaccharides, therefore forms the crosslinked polymer matrix of the hydrogel particles. Other mixtures of oppositely charged polysaccharides are contemplated, such as a mixture of chitosan and alginate.

In some embodiments, a charged polysaccharide that is capable of interacting with another polysaccharide of opposite charge may be regarded herein as a crosslinking agent.

In some other embodiments, when the hydrogel particles comprise a glycosaminoglycan (GAG), the GAG may not form part of the crosslinked network structure of the hydrogel polymer. In such embodiments, the GAG may be present as an additive component in the hydrogel particles. As an additive, the glycosaminoglycan may act to help modify the physical or mechanical properties of the hydrogel particles.

In particular, the glycosaminoglycan (GAG) can enable the hydrogel particles to become more pliable, with greater plastic like properties. This may be beneficial when the hydrogel particles also comprise an aqueous insoluble alkaline earth metal phosphate as described below, as the inclusion of a glycosaminoglycan (GAG) in the particles may enable the mechanical properties of the particles to be adjusted so as to improve structural stability and in vivo performance. Changes in hydrogel particle properties may be due to the glycosaminoglycan acting to prevent crystallisation and growth of the alkaline earth metal phosphate, thereby reducing the rigidity of the particles.

In one set of embodiments, hydrogel particles comprising a glycosaminoglycan may comprise chondroitin sulphate in an amount of up to 2% (w/v). In some embodiments, the hydrogel particles may comprise chondroitin sulphate in an amount of up to 1% (w/v).

When the hydrogel particles comprise a crosslinked macromolecule composed of electrostatically linked chondroitin sulphate and chitosan, the amount of chondroitin sulphate and chitosan may preferably be in a 1:2 weight ratio. An injectable formulation containing such hydrogel particles can be prepared by emulsifying a an aqueous solution containing 2% (w/v) chitosan with an oil, to which a second aqueous solution containing 1% (w/v) chondroitin sulphate is added under continuous shear to give 1:2 chondroitin sulphate:chitosan weight ratio microhydrogel particles in a water-in-oil emulsion.

If desired, the hydrogel particles may comprise one or more additional components. The additional components may be used to modify the chemical and/or physical properties of the hydrogel particles present in the injectable composition of the invention.

In one form, the hydrogel particles may further comprise a biocompatible aqueous insoluble alkaline earth metal phosphate and/or a biocompatible proteoglycan.

Aqueous insoluble alkaline earth metal phosphates may be included in the hydrogel particles to modify the physical or mechanical properties of the hydrogel particles. For instance, the aqueous insoluble alkaline earth metal phosphates may be used to increase the rigidity to the particles.

In some embodiments, the hydrogel particles may comprise aqueous insoluble phosphates of calcium and magnesium. Doped calcium phosphates, such as $Mg^{2+}$, $Zn^{2+}$, $Na^+$, $CO_3^{2-}$ and $SiO_4^{4-}$ doped calcium phosphates, are also contemplated.

In one embodiment the aqueous insoluble alkaline earth metal phosphate is apatite.

Apatite is a group of phosphate minerals and includes fluorapatite, $Ca_5(PO_4)F_3$; chlorapatite, $Ca_5(PO_4)_3Cl$; bromapatite, $Ca_5(PO_4)_3Br$ and hydroxyapatite, $Ca_5(PO_4)_3(OH)$ (which are also often usually written $Ca_{10}(PO_4)_6(OH, F, Cl, Br)_2$ to denote that the crystal unit cell comprises two molecules). Hydroxyapatite crystallizes in the hexagonal crystal system. It has a specific gravity of 3.1-3.2 and has a hardness of 5 on the Mohs hardness scale. Hydroxyapatite can be found in teeth (enamel) and bones. About 70% of bone is comprised of hydroxyapatite.

In a preferred embodiment the hydrogel particles may further comprise hydroxyapatite.

In one set of embodiments, the hydrogel particles may comprise hydroxyapatite in an amount of up to 0.1% (1 mg/ml).

In one set of embodiments, the hydrogel particles may comprise hydroxyapatite and chitosan at a weight ratio of hydroxyapatite to chitosan of 3:20, more preferably a weight ratio of 1:20 hydroxyapatite:chitosan. The latter ratio can be achieved using an aqueous 2% chitosan solution containing hydroxyapatite at a concentration of 1 mg/mL in the preparation of the injectable composition of the invention.

Hydroxyapatite may also be capable of modifying crosslinking reactions used to form the crosslinked polymer of the hydrogel particles through charge interactions with one or more components of the crosslinked polymer. For example, excess of $PO_4^{3-}$ ions from hydroxyapatite at mildly acidic pH may modify the ability of chitosan to interact with a crosslinking agent.

Proteoglycans are a specific group of compounds that have at least one glycosaminoglycan chain attached to a protein. Such compounds may comprise multiple negative charges at physiological pH (approximately pH 7). The hydrogel particles may comprise at least one proteoglycan. Mixtures of two or more proteoglycans are also contemplated. An example of a proteoglycan is aggrecan.

In one set of embodiments, the hydrogel particles may be porous. In such embodiments, one or more of the hydrogel particles in the injectable composition comprises at least one pore and may comprise a plurality of pores. In one form, each hydrogel particle comprises a plurality of pores. Pores in the hydrogel particles may help to modify the release of the biologically active agent that is in the particles. In some embodiments, hydrogel particles comprising pores may release biologically active agent present therein at a faster rate.

Hydrogel particles in the injectable composition of the invention may be uncoated hydrogel particles or coated hydrogel particles. The injectable composition may comprise a mixture of uncoated and coated hydrogel particles.

In one set of embodiments, the injectable composition comprises one or more coated hydrogel particles. Thus hydrogel particles as described herein may be coated. The injectable composition of the invention may therefore comprise at least one coated hydrogel particle in the aqueous phase. In some embodiments, the injectable composition of the invention may comprise a plurality of coated hydrogel particles in the aqueous phase.

Coated hydrogel particles may comprise an inner hydrogel component forming a core and an outer component of material that covers at least a portion of the core. The outer component can be regarded as a coating for the inner core.

The coating of a coated hydrogel particle may be a distinct layer of material that covers at least a portion of a hydrogel core. In some embodiments, the coating may be a shell that encapsulates and contains the hydrogel core.

When present, the coating generally forms part of the hydrogel particle per se and is attached to the inner core of the particle. Attachment of the coating to the core may be via physical or chemical means.

The presence of a coating may be determined using various optical, imaging or spectroscopic techniques. For example, the coating may be visually observed microscopically.

It is thought that the coating forms due to phase separation of a component material from the mixture of components used to form the injectable composition of the invention in accordance with methods described herein. The separated component material preferentially locates at the surface to form the coating while the remaining components of the mixture can form the core of the hydrogel particle.

As an example, a coated hydrogel particle with a polysaccharide coating may be formed when a crosslinker diffuses from the core microhydrogel to the surface of the core and reacts with a polysaccharide in solution in the environment to give a crosslinked gel layer around the core.

In another example, a coated hydrogel particle may be formed when two oppositely charged polymers interact electrostatically to form an interpenetrated network (IPN), where one of the polymers is located in the core of the hydrogel and the other polymer is located in solution in the microhydrogel environment.

In one set of embodiments, the coating may be attached to a microhydrogel particle core by chemical means. Exemplary chemical means can be chemical bonds that may be formed between the coating and the hydrogel particle core.

In some embodiments, at least a portion of the coating is bound to at least a portion of the polymer material component in the hydrogel core via covalent or non-covalent bonds. Non-covalent bonds may be electrostatic bonds or hydrogen bonds.

In another set of embodiments, the coating may be attached to a microhydrogel particle core via physical means. In some embodiments, at least a portion of the coating is physically interlaced with at least a portion of the polymer material component in the hydrogel particle core on a molecular scale. In some embodiments, a portion of the coating is physically entangled with a portion of the polymer material of the hydrogel core. The region of entanglement between the coating and the hydrogel particle core can resemble an interpenetrating polymer network.

The coating can advantageously help to control the passage of the biologically active agent from the hydrogel particle into the aqueous liquid portion of the aqueous phase of the water-in-oil emulsion and hence into the surrounding environment for release in vivo. In some embodiments, the coating can assist to reduce the rate of release of the biologically active agent from the hydrogel particle and thus help retard premature release of the active agent, or help promote sustained release of the active agent over a period of time.

Control over the passage of the biologically active agent may be achieved through a number of mechanisms, including by the coating per se, having adjustable porosity, or by the coating carrying a net charge.

The coating of a coated hydrogel particle may further be crosslinked or non-crosslinked. The degree of crosslinking (if any) may provide a further mechanism for controlling the passage of a biologically active agent from the hydrogel particle.

A coating of a coated hydrogel particle may comprise or be composed of a biocompatible material.

In some embodiments, the coating may comprise a biocompatible polymer material. Such polymer materials can be biocompatible, hydrophilic and amenable to aqueous solvation. A range of biocompatible polymers may be suitable for the coating.

In one embodiment, the coating may comprise a polysaccharide. The polysaccharide may be selected from any one of the polysaccharides described herein. In one form, the coating comprises a polysaccharide selected from the group consisting of chitosan, alginate, hyaluronic acid, chondroitin sulphate, cellulose, dermatan sulphate, keratan sulphate and heparin sulphate, as well as salts thereof and derivatives thereof. Such polysaccharides, salts and derivatives thereof are described herein.

In some embodiments it can be preferable for the polysaccharide in the coating to be different from the polysaccharide in the core of the hydrogel particle. For example, when a hydrogel particle core comprises a crosslinked chitosan, the coating may comprise alginate or a glycosaminoglycan such as chondroitin sulphate. Similarly, when the hydrogel particle core comprises a crosslinked alginate or crosslinked chondroitin sulphate, the coating on the hydrogel particle core may comprise chitosan. Other combinations of polysaccharide are also contemplated.

At physiological pH (approximately pH 7), polysaccharides may carry a net charge, which depending on the composition of the polysaccharide, may be positive or negative. Consequently, a coating comprising such polysaccharides may be charged at physiological pH. The charged coating can influence the rate of release of a biologically active agent from the hydrogel particle, particularly where the active agent is also charged. For example, a coating having a net negative charge may interact with a positively charged biologically active agent electrostatically and in this manner can help to modulate the passage of the active agent from the hydrogel particle into the aqueous liquid of the aqueous phase (i.e. syneresis).

In some embodiments, the coating may comprise a polysaccharide that is positively charged at physiological pH. The positively charged polysaccharide can impart a positive charge to the coating. An exemplary positively charged polysaccharide is chitosan.

When chitosan is present in the coating, the core of the hydrogel particle may and preferably will comprise a different polysaccharide, which is not chitosan. In one preference, the hydrogel particle core comprises negatively charged polysaccharide such as alginate or a glycosaminoglycan such as chondroitin sulphate. The negatively charged polysaccharide may aid in the attachment of the positively charged coating to the core component of the hydrogel particle.

In one embodiment, the coating comprises a polysaccharide that is negatively charged at physiological pH. The negatively charged polysaccharide can impart a negative charge to the coating. Exemplary negatively charged polysaccharides may be selected from alginate and sulphated glycosaminoglycans (sulphated GAG's). Sulphated GAGs may be chondroitin sulphate, keratan sulphate, dermatan sulphate and heparin sulphate. When the coating comprises a negatively charged polysaccharide, in some embodiments it can be preferable for the core of the hydrogel particle to comprise a positively charged polysaccharide. In one preference, the hydrogel particle core comprises chitosan. The positively charged polysaccharide may aid in the attachment of the negatively charged coating to the core of the hydrogel particle.

A coating of a coated hydrogel particle may be crosslinked or non-crosslinked. A crosslinked coating may comprise a crosslinked polysaccharide, while a non-crosslinked coating may comprise a polysaccharide that is not crosslinked.

Non-crosslinked and crosslinked coatings may be attached to a hydrogel particle core via physical or chemical means as described herein.

Crosslinked polysaccharides suitable for use in a crosslinked coating may comprise a polysaccharide as described herein crosslinked with a suitable crosslinking agent. A skilled person would be able to select a suitable crosslinking agent for a selected polysaccharide. Exemplary polysaccharides include chitosan, alginate and sulphated GAGs such as chondroitin sulphate and suitable crosslinking agents for these polysaccharides are described herein.

In some embodiments, when the coating comprises a charged polysaccharide (either positively or negatively charged), the hydrogel particle core may comprise a charged compound that is capable of interacting with the charged polysaccharide in the coating in order to facilitate attachment of the coating to the core. The charged compound may be selected to be complementary to the charged polysaccharide in the coating. For instance, a positively charged compound may be incorporated in the hydrogel particle core when a negatively charged polysaccharide is in the coating, and vice versa.

In one embodiment, the coating comprises chitosan. In such embodiments, the hydrogel particle may comprise a phosphate compound. The phosphate compound can interact with amino groups present in chitosan in order to attach the chitosan to the hydrogel through non-covalent electrostatic bonds. The phosphate compound may be tripolyphosphate, and salts thereof, such as sodium tripolyphosphate (TPP) and potassium tripolyphosphate. In one preference, the phosphate compound is TPP.

In one embodiment, the coating comprises alginate or a sulphated glycosaminoglycan such as chondroitin sulphate. In such embodiments, the hydrogel particle core may comprise a cation, preferably a divalent cation. Exemplary cations may be calcium ($Ca^{2+}$) or magnesium ($Mg^{2+}$) cations. The cation in the hydrogel particle core can interact with anionic groups such as carboxylic acid or sulphate groups present in polysaccharide in order to attach the polysaccharide to the core.

When a charged compound is used to facilitate the attachment of a coating to the hydrogel particle core, it may not be necessary for the polymer (e.g. the polysaccharide) in the core of the hydrogel particle to be charged. For example, the hydrogel core may comprise or be composed of an uncharged polysaccharide. In these circumstances, the anchoring of the coating to the hydrogel particle core is achieved via the charged compound contained in the core.

Additionally, when a hydrogel particle comprises a charged compound (such as a phosphate compound or a divalent cation), the charged compound may diffuse from the core of the hydrogel particle into the coating. Depending on the polysaccharide in the coating, the charged compound may act as a crosslinking agent for the polysaccharide and in this way help promote the formation of a crosslinked polysaccharide in the coating. A crosslinked coating may have greater thickness than a non-crosslinked coating and thus might provide a further avenue for modulating the sustained release of a biologically active agent from the coated hydrogel particle over a period of time.

Crosslinked polysaccharides useful for a coating in a coated hydrogel particle may comprise polysaccharide and a crosslinking agent in a suitable molar ratio. In some embodiments, it may be desirable to vary the level of crosslinking by adjusting the molar ratio of polysaccharide to crosslinking agent. Variation in the crosslink density may be used to modify the physical properties of the coating, such as the porosity or the net charge of the coating. In turn, this may help to modulate the release of a bioactive agent from the hydrogel particle to the aqueous liquid portion of the aqueous phase of the injectable composition.

In some embodiments, it may be preferable for a crosslinked polysaccharide in the coating to comprise a relatively low crosslinking ratio (i.e. a low molar concentration of crosslinking agent) as this may result in ionised groups in the polysaccharide remaining charged at physiological pH and thus available to participate in non-covalent interactions with a biologically active agent contained in the hydrogel particles. Non-covalent interactions between the biologically active agent and the coating can also help to modulate the release profile of the biologically active agent from the hydrogel particle over a period of time.

In some embodiments, the molar ratio of crosslinking agent to polysaccharide in a coating comprising a crosslinked polysaccharide is from about 1:1 to about 50:1, preferably from about 2:1 to about 30:1, more preferably from about 5:1 to about 20:1.

In some embodiments, the coating of a coated hydrogel particle may comprise an amphiphilic compound. An amphiphilic compound in the coating may help to stabilise the water-in-oil emulsion or may help to modulate the release of the biologically active agent from the injectable composition of the invention. In one embodiment, the amphiphilic compound is a lecithin.

In some embodiments, the coating of a coated hydrogel particle is porous. Porous coatings may be formed through the incorporation of a porogen during the manufacture of the injectable composition of the invention or by varying crosslinked density in the case of a crosslinked coating.

Porogens of different size may be used to produce coatings of different porosity. An exemplary porogen is poly (ethylene glycol) (PEG). PEG compounds of different molecular weight can produce passages (pores) of different size in the coating. Exemplary poly(ethylene glycol) may have a molecular weight in a range of from about 200 to 100,000 Da.

The injectable composition of the invention comprises at least one biologically active agent, which is desired to be administered to a subject.

As used herein, the term "biologically active agent" encompasses any molecule of synthetic or natural origin, which is able to elicit a desired physiological effect in vivo. For example, a biologically active agent may be a drug compound or a vaccine having use in the treatment or prevention of a disease or condition, especially one in which the delivery of an immediate dose is desired followed by prolonged delivery over a period of time to a subject.

In accordance with the invention, the injectable composition comprises a biologically active agent in the aqueous phase of the water-in-oil emulsion. More particularly, the biologically active agent is contained in the aqueous liquid and in the hydrogel particles of the aqueous phase. Accordingly, it may be considered that two phases of the injectable composition comprise the biologically active agent. It is believed that the presence of the biologically active agent in the aqueous liquid and in the hydrogel particles facilitates the ability of the injectable composition to provide for rapid and sustained delivery of the active agent, as further described below.

When the injectable composition comprises coated hydrogel particles, the biologically active agent may be situated in the core or in the coating of the hydrogel particles. In some embodiments, the biologically active agent may be situated in both the core and the coating of the coated hydrogel particles.

The injectable composition of the invention may comprise a range of biologically active agents.

In some embodiments, hydrophilic biologically active agents may be preferred.

The biologically active agent may be selected from non-limiting classes of active agents including hormones, antimicrobials, therapeutic antibodies, cytokines, fusion proteins, antigens, viruses, bacteria, bacteria fragments, vaccines and hormones. The injectable composition of the invention may comprise one or more biologically active agents selected from one or more of these classes.

Biologically active agents may carry a net charge at physiological pH, which can be indicated by the isoelectric point (pI) of the active agent. Alternatively, biologically active agents may have no net charge (i.e. neutral).

When the injectable composition comprises two or more biologically active agents, the biologically active agents may belong to the same class of active agent or to different classes of active agent. Each biologically active agent may also be independently selected at each occurrence.

Hormones may be peptide hormones such as insulin and somatotropin, or steroid hormones such as corticosteroids, estrogens, progestogens and androgens.

A "peptide hormone" is a peptide or protein that has an effect on the endocrine system of a subject.

A specific example of a peptide hormone that may be contained in and delivered by the injectable composition of the invention is somatotropin. Somatotropin stimulates the growth, cell reproduction and cell regeneration in humans and non-human animals and is important in growth and development.

Therapeutic antibodies may be infliximab, adalimumab, nituximab, alemtuzumab, daclizumab or basiliximab.

Fusion proteins may be etanercept.

An "antigen" is a compound which, when introduced into a human or non-human animal, will result in the formation of antibodies against the antigen and cell-mediated immunity.

Antigens are commercially available or may be prepared using known procedures and techniques. Representative antigens may include, but are not limited to, natural, recombinant or synthetic products derived from viruses, bacteria, fungi, parasites and other infectious agents including prions. Examples of antigens also include human antigens which might be desirable to use in prophylactic or therapeutic vaccines e.g. which are involved in or relevant to autoimmune diseases, in particular autoantigens; hormones; tumour antigens; and allergens. The microbial (e.g. viral or bacterial) products can be components which the organism produces or can be induced to produce e.g. by enzymatic cleavage or can be components of the organism that were produced by recombinant DNA techniques that are well known to those of ordinary skill in the art.

Some specific examples of antigens that may be contained in and delivered by the injectable composition of the invention are TSOL18 antigen, Bm86 antigen, H. contortus antigen, antigens for Old World Screwworm fly (*Chrysomya bezziana*) and antigens for bluetongue virus.

A "vaccine" is a preparation that is used to stimulate the immune system to produce antibodies against one or more specific agents. The vaccine may prevent, treat or suppress the progression of a condition, disease or disorder that is caused directly or indirectly or exacerbated by an infectious or infecting agent or any other agent.

One specific vaccine that may be contained in and delivered by the injectable composition of the invention is luteinizing hormone-releasing hormone (LHRH) vaccine. The vaccine may be used to suppress reproduction in animals and form the basis for immunocastration or immunocontraception.

In one form, the injectable composition comprises one or more biologically active agents selected from the group consisting of vaccine antigens and hormones.

In some embodiments, the injectable composition of the invention comprises an adjuvant. The term "adjuvant" as used herein refers to a compound or substance that enhances a subject's physiological response to a biologically active agent. For example, in the case of an antigen, an adjuvant may act to enhance a subject's immune response to the antigen by increasing antibodies and thus the longevity of the immune response.

An adjuvant can therefore help to promote a more effective physiological response to a biologically active agent in a subject, compared to the administration of the biologically active agent alone or without the adjuvant.

In some embodiments, an adjuvant may act to modify the release of a biologically active agent in vivo. The modulated release can provide a more durable or higher level of delivery using smaller amounts or fewer doses of the biologically active agent, compared to if the biologically active agent were administered alone or without the adjuvant.

The adjuvant can be present in the water-in-oil emulsion of the injectable composition and may be in the oil phase or in the aqueous phase of the emulsion. In some embodiments of the injectable composition, the oil phase and aqueous phase of the emulsion may each comprise an adjuvant.

In one embodiment of the injectable composition, the aqueous phase of the water-in-oil emulsion comprises at least one adjuvant. In such embodiments, the adjuvant is preferably hydrophilic and may be water soluble.

When present in the aqueous phase, the adjuvant may be in the aqueous liquid and/or in the hydrogel particles of the aqueous phase. For example, the adjuvant may be dissolved in the aqueous liquid of the aqueous phase. Additionally or alternatively, the adjuvant may be contained in the hydrogel particles or be incorporated as part of the chemical composition or structure of the hydrogel particles of the aqueous phase. For example, chitosan may have adjuvanting properties and thus an adjuvant may be introduced into the injectable composition through the use of hydrogel particles comprising crosslinked chitosan in the aqueous phase.

Hydrophilic adjuvants that may be incorporated in the aqueous phase of the water-in-oil emulsion may be selected from the group consisting of alum, the water soluble extract of *Mycobacterium smegmatis*, synthetic N-acetyl-muramyl-1-alanyl-d-isoglutamine, monoacyl lipopeptides and ligands for Toll-like receptors. Such adjuvants may be incorporated in the aqueous liquid and/or within hydrogel particles of the aqueous phase.

In other embodiments of the injectable composition, the oil phase of the water-in-oil emulsion comprises at least one adjuvant. In such embodiments, the adjuvant is preferably lipophilic and is at least oil compatible and may be oil soluble.

In some embodiments, the oil per se can be an adjuvant and thus the oil phase comprises an adjuvanting oil. The use of an adjuvanting oil may be desirable as it avoids the need to incorporate a separate adjuvanting compound in the injectable composition of the invention. Examples of adjuvanting oils are described herein.

In alternative embodiments, the oil phase may comprise a lipophilic adjuvant dissolved or suspended in a non-adjuvanting (passive) oil.

Various adjuvants are known to those skilled in the art. Adjuvants useful for the injectable composition of the invention may be inorganic adjuvants or organic adjuvants.

A skilled person would appreciate that the selection of a particular adjuvant might depend on the biologically active agent to be delivered to a subject, the disease or disorder to be treated by the active agent, and the release profile desired for the active agent.

Some examples of specific adjuvants include incomplete Freunds adjuvant (IFA), Adjuvant 65 (containing peanut oil, mannide monooleate and aluminium monostearate), oil emulsions, Ribi adjuvant, the pluronic polyols, polyamines, Avridine, Quil A, saponin, MPL, QS-21, mineral gels, and aluminium salts such as aluminium hydroxide and aluminium phosphate. Other examples include oil-in-water emulsions such as SAF-1, SAF-0, MF59, Seppic ISA720, and other particulate adjuvants such as ISCOMs and ISCOM matrix.

The injectable composition of the invention may optionally comprise one or more additional components. The additional components may be, for example, salts or ions to adjust the pH or ionic strength of the aqueous phase, surfactants, emulsifiers, and the like. When present, the additional components may be contained in the oil phase and/or the aqueous phase of the water-in-oil emulsion described herein, including in the hydrogel particles and/or the aqueous liquid of the aqueous phase. A skilled person would understand that the additional components may be dissolved or suspended in the oil phase or aqueous phase, depending on the lipophilicity or hydrophilicity of a particular component.

In one set of embodiments, the injectable composition of the invention may comprise at least one surfactant. Surfactants may help to reduce or prevent complete phase separation of the aqueous and oil phases and thus aid in the production of a more stable water-in-oil emulsion.

Surfactants may be present in an amount of up to 5% by weight of the injectable composition. In some embodiments, the surfactant may be present in an amount of up to 1% by weight of the injectable composition.

Surfactants utilised in the injectable composition of the invention may have a low hydrophilic-lipophilic balance (HLB) value. For instance, the surfactant may have a HLB of 6 or less. Additionally, surfactants with high HLB ratio may be used in combination with low HLB surfactants to give low HLB surfactant mixture to optimise the stability of the water-in-oil emulsion.

Various pharmaceutically acceptable surfactants are known to one skilled in the art. Pharmaceutically acceptable surfactants may be anionic, cationic, zwitterionic or non-ionic.

In one set of embodiments, the injectable composition of the invention further comprises a non-ionic surfactant. A range of non-ionic surfactants may be employed. Exemplary non-ionic surfactants may be selected from sorbitan esters, polysorbates and poloxamers.

Preferred surfactants may be selected from Tween 80 (Polysorbate 80), glycol and glycerol esters, polyoxyethylene/propylene glycols such as PEG-35 castor oil, sorbitan derivatives such as polysorbates-20, 40, 60, 65, 80 and 85, sorbitan monooleate, sorbitan monolaurate, sorbitan monopalmitate, sesquioleate, trioleate, tristearate, saccharide and polysaccharide based surfactants.

The injectable composition of the invention can be prepared using equipment and techniques suitable for forming emulsion compositions, in particular, water-in-oil emulsions.

In one aspect, the present invention provides a process for preparing an injectable composition for rapid and sustained delivery of a biologically active agent, the process comprising the steps of:

providing a first aqueous composition comprising a first hydrogel forming component and a second aqueous composition comprising a second hydrogel forming component, at least one of the first aqueous composition and the second aqueous composition comprising a biologically active agent;

combining the first aqueous composition with a lipophilic composition comprising an oil to form an emulsified composition; and combining the second aqueous composition with the emulsified composition under conditions allowing the first hydrogel forming component to react with the second hydrogel forming component to form a plurality of hydrogel particles in situ and thereby provide an injectable composition comprising a water-in-oil emulsion comprising an aqueous phase dispersed in an oil phase, the aqueous phase comprising a plurality of hydrogel particles and an aqueous liquid, and wherein the biologically active agent is contained in the hydrogel particles and in the aqueous liquid of the aqueous phase of the water-in-oil emulsion.

In forming the injectable composition, the first hydrogel forming component is one selected from a polymer and a crosslinking agent while the second hydrogel forming component is the other selected from a polymer and a crosslinking agent. That is, when the first hydrogel forming component is selected to be a polymer, then the second hydrogel forming component is a crosslinking agent, and vice-versa. Polymers and crosslinking agents suitable for forming hydrogel particles have been described herein.

The aqueous compositions and the lipophilic composition may be combined under shear, to form the hydrogel particles and the water-in-oil emulsion.

In one embodiment, the injectable composition of the invention may be prepared by initially combining a first aqueous composition comprising a polysaccharide in an aqueous solvent with a lipophilic composition comprising a physiologically acceptable oil and a surfactant, and emulsifying the first aqueous composition in the lipophilic composition under shear. A second aqueous composition comprising a crosslinking agent in an aqueous solvent is then combined with the initial emulsified mixture with continuous agitation or shear. The crosslinking agent reacts with the polysaccharide and spontaneously crosslinks the polysaccharide to result in colloidal portions of crosslinked hydrogel being formed in situ. The resulting composition is therefore a water-in-oil emulsion containing a plurality of hydrogel particles. The formed hydrogel particles are dispersed in the aqueous solvent, which forms the aqueous liquid portion of the aqueous phase of the emulsion. Crosslinking of the polysaccharide and the formation of hydrogel particles containing the crosslinked polysaccharide occurs without the need for additional curing mechanisms or apparatus (e.g. by UV, IR, heat). Crosslinking and hydrogel particle formation may occur rapidly.

Advantageously, it has been found that the resulting injectable composition is stable, with the water-in-oil emulsion and the dispersion of hydrogel particles in the emulsion remaining stable over a number of weeks. In general, a stable emulsion would not exhibit phase separation, aggregation or precipitation of the composition components over a desired period of time. In one set of embodiments, the injectable composition of the invention may be stable for more than 6 months at ambient room temperature.

The order in which the aqueous compositions containing the crosslinking agent and polysaccharide are mixed with the lipophilic composition may be reversed. That is, the first aqueous composition may comprise a crosslinking agent (e.g. TPP) and the lipophilic composition comprising the oil may initially be emulsified with the crosslinking agent containing aqueous composition. Subsequently, a second aqueous composition comprising a polysaccharide (e.g. chitosan) may then be added to this initial emulsified composition to produce the injectable composition of the invention.

In some embodiments, when the hydrogel particles comprise a mixture of polysaccharides, the injectable composition may be prepared by initially combining a first aqueous composition comprising a first polysaccharide in an aqueous solvent with a lipophilic composition comprising a physiologically acceptable oil, and emulsifying the first aqueous composition in the lipophilic composition under shear. A second aqueous composition comprising a second polysaccharide in an aqueous solvent is then combined with the initial emulsified mixture with continuous agitation or shear. Preferably, the second polysaccharide is of opposite charge to the first polysaccharide. The first and second polysaccharides then crosslink via intermolecular electrostatic interactions to result in colloidal portions of crosslinked hydrogel being formed in situ.

In some embodiments, an aqueous composition used in the preparation of the injectable composition may comprise a mixture of hydrogel forming components of similar electrostatic charge. For instance, an aqueous composition may comprise a mixture of negatively charged polysaccharides such as alginate and chondroitin sulphate. If desired, such aqueous compositions can also include an ionic crosslinking agent with the same charge, such as TPP. An initial emulsion containing this aqueous composition can be combined with another aqueous composition containing a hydrogel forming component of opposite charge, for example, a positively charged polysaccharide such as chitosan. In desired, the chitosan constituent may comprise other positively charged polymers and/or crosslinker species. Combining these different aqueous compositions containing components of opposite charge in an emulsion can then allow formation of an injectable composition comprising microhydrogel particles having a combination of different polysaccharides that are crosslinked electrostatically.

During production of the injectable composition, formation of the hydrogel particle by crosslinking a hydrogel forming polymer in the presence of the biologically active agent can involve two processes: formation of the crosslinked hydrogel network and compression of the network driven by increasing crosslink density, which continues until the balance between the osmotic and elastic forces of the polymer chains is reached. The aqueous liquid phase expelled by the reduction in volume of the hydrogel during crosslinking, termed syneresis liquid, contains free bioactive species not physically bound or encapsulated by the hydrogel polymer chains, i.e. those exceeding the binding capacity of the crosslinked chains. Notably, the binding capacity of the crosslinked polymer chains may be lower than that of the chains prior to crosslinking due to entropic conformational changes imposed on the component arising from compression during network formation. The physical equilibrium established between (i) bioactive species bound to the hydrogel polymer chains and (ii) free species in aqueous liquid where the aqueous liquid is both external to the hydrogel network in the aqueous phase of the emulsion and within the swollen hydrogel itself, is characterised by the respective binding coefficient of the system.

In embodiments where the injectable composition comprises coated hydrogel particles, the first aqueous composition and the second aqueous composition used in the preparation of the injectable composition may each optionally further comprise a coating forming component. In one embodiment, the second aqueous composition comprises a coating forming component. In a further embodiment, both the first aqueous composition and the second aqueous composition comprise coating forming components.

When the first aqueous composition is emulsified with the lipophilic composition and the resulting emulsion subsequently combined with the second aqueous composition, the first and second hydrogel forming components react to form hydrogel particles in situ in the composition. Meanwhile, the coating forming component that is also present in the emulsified reaction mixture forms a coating that at least partially covers the surface of one or more of the hydrogel particles. The coating is thus also formed in situ on the surface of the hydrogel particles.

As an example, the injectable composition of the invention may be prepared by initially combining a first aqueous composition comprising a first hydrogel forming component with a lipophilic composition comprising a physiologically acceptable oil and a surfactant, and emulsifying the first aqueous composition and the lipophilic composition under shear. A second aqueous composition comprising a second hydrogel forming component and a coating forming component in an aqueous solvent is then combined with the initial emulsified mixture with continuous agitation or shear. The first hydrogel forming component reacts with the second hydrogel forming component to result in colloidal portions of hydrogel being formed in situ while the coating forming component forms a coating on the colloidal hydrogel. The coating is located at the surface of the hydrogel particle. A portion of the coating may be physically interlaced with the underlying hydrogel particle core to attach the coating to the hydrogel core. Alternatively, the coating may be attached (e.g. chemically attached) to the underlying hydrogel core. The resulting composition is therefore a water-in-oil emulsion containing one or more coated hydrogel particles dispersed in the aqueous liquid portion of the aqueous phase of the emulsion.

As described herein, in some embodiments a crosslinked coating may be formed on the hydrogel particles. In such embodiments, a coating forming component may be incorporated in each of the aqueous compositions used to form the injectable composition of the invention. The coating forming components react together to form a crosslinked coating.

As an example, the injectable composition of the invention may be prepared by initially combining a first aqueous composition comprising a first hydrogel forming component and a first coating forming component with a lipophilic composition comprising a physiologically acceptable oil and a surfactant. The mixture is then emulsified under shear. A second aqueous composition comprising a second hydrogel forming component and a second coating forming component in an aqueous solvent is then combined with the initial emulsified mixture with continuous agitation or shear. The first hydrogel forming component reacts with the second hydrogel forming component to form colloidal portions of hydrogel in situ. Meanwhile, the first coating forming component reacts with the second coating forming component to form a crosslinked coating in situ on the colloidal hydrogel.

Where a crosslinked coating is desired to be formed, it is preferable that the components in each of the first aqueous composition and the second aqueous composition do not react with one another. Rather, it is preferred that reaction between the components in these compositions only takes place after the first and second aqueous compositions are combined together and emulsified with the lipophilic composition.

In the above described processes, one or more compositions selected from the group consisting of the first aqueous composition, the second aqueous composition and the lipophilic composition may comprise an adjuvant. Accordingly, an adjuvant may be contained in at least one of the aforementioned compositions used to prepare the injectable composition of the invention.

In one embodiment, the lipophilic composition comprises an adjuvant. Such embodiments would result in the injectable composition of the invention comprising an adjuvant in the oil phase of the water-in-oil emulsion.

In one embodiment, the lipophilic composition comprises a physiologically acceptable adjuvanting oil. Examples of adjuvanting oils are described herein.

In one embodiment, the lipophilic composition comprises a physiologically acceptable passive oil and at least one lipophilic adjuvanting compound or substance that is dissolved or dispersed in the passive oil.

In some embodiments an adjuvant may be provided by at least one adjuvanting compound or substance being dissolved in or dispersed in the first aqueous composition and/or the second aqueous composition used to prepare the injectable composition. Such adjuvanting substances are generally hydrophilic. Examples of hydrophilic adjuvanting compounds are described herein.

As an illustration with reference to one of the embodiments described herein, a first aqueous composition comprising chitosan may be combined with a lipophilic composition comprising an adjuvanting oil (e.g. Montanide ISA61) under agitation or shear. A second aqueous composition comprising sodium tripolyphosphate (TPP) is then added to the resulting emulsified composition in order to crosslink the chitosan. The addition of the TPP to the initial composition occurs dropwise, under continuous shear. A uniform water-in-oil emulsion formulation that comprises colloidal portions of hydrogel composed of crosslinked chitosan in the aqueous phase of the emulsion is then formed.

As an illustration of a further embodiment described herein, when coated hydrogel particles are desired, a first aqueous composition comprising alginate and sodium tripolyphosphate (TPP) may be combined with a lipophilic composition comprising an adjuvanting oil (e.g. Montanide ISA61) under agitation or shear. A second aqueous composition comprising chitosan and calcium chloride ($CaCl_2$) is then added to the resulting emulsified composition under continuous shear. Calcium cations interact with the alginate to crosslink the alginate and form colloidal portions of alginate-$Ca^{2+}$ hydrogel. Meanwhile, chitosan is crosslinked with TPP to produce a crosslinked chitosan coating on the colloidal hydrogel. The resulting composition is a water-in-oil emulsion formulation comprising colloidal portions of coated hydrogel in the dispersed aqueous phase. The coated hydrogel is composed of crosslinked alginate core and a crosslinked chitosan coating When preparing the injectable composition of the invention, the biologically active agent may be contained in the first aqueous composition and/or in the second aqueous composition described herein. In one preference, the first aqueous composition comprises the biologically active agent. The inclusion of the biologically active agent in the first aqueous composition may be preferred as this may promote more efficient distribution of the active agent in the emulsion and consequently, in the final injectable composition.

The first aqueous composition, the lipophilic composition and the second aqueous composition may be combined in any suitable volumetric ratio. In one specific embodiment, the first aqueous composition comprises a crosslinking agent and a biologically active agent, the lipophilic composition comprises an adjuvanting oil and the second aqueous solution comprises a polysaccharide and the volumetric ratio between the first aqueous composition:lipophilic composition:second aqueous composition is 0.5:1.2:1.8.

During the preparation of the injectable composition, a portion of the biologically active agent becomes encapsulated in the hydrogel particles that are formed in situ. A further portion of the biologically active agent is not encapsulated in the hydrogel particles but remains in the aqueous solvent, which then forms the aqueous liquid of the aqueous phase of the water-in-oil emulsion.

As the hydrogel particles comprising the biologically active agent are prepared ex vivo, product reproducibility may be improved.

If other components are desired to be present in the injectable composition, such components may be incorporated in one or more of the first aqueous composition, the second aqueous composition and/or in the lipophilic composition used to prepare the injectable composition. For example, in one embodiment, an aqueous insoluble alkaline earth metal phosphate such as hydroxyapatite may be incorporated in the aqueous composition comprising the polysaccharide, while a biocompatible proteoglycan may be incorporated in the aqueous composition comprising the crosslinking agent.

If porous hydrogel particles are desired, one or more of the first aqueous composition, the second aqueous composition and/or the lipophilic composition used to prepare the injectable composition may further comprise a porogen.

In some embodiments, at least one selected from the first aqueous composition and the second aqueous composition comprises a porogen.

A porogen is a substance that can be used to form an opening or pore in a material. Since the porogen is used to form pores in the hydrogel particles, it can be preferable for the porogen to be a hydrophilic substance.

The reaction between a polymer and a crosslinking agent to form hydrogel particles may proceed in the presence of a porogen. The porogen does not participate in the hydrogel forming reaction and thus the hydrogel material forms around the porogen. Accordingly, the porogen acts as a template for the pores in the hydrogel particles. After the hydrogel particles are formed, the porogen may leach from the particles and be removed, thereby leaving pores in the hydrogel particles.

A range of porogens may be employed to form porous hydrogel particles. An example of a suitable porogen is poly(ethylene glycol) (PEG). A skilled person would understand that PEG is a hydrophilic polymer that is compatible with an aqueous solvent.

Poly(ethylene glycol) is useful as a porogen and may have a molecular weight in a range of from about 200 to 100,000 Da. In one embodiment, the poly(ethylene glycol) has a molecular weight of about 35,000 Da.

Porogens for forming porous hydrogel particles may be used in a suitable amount. The quantity of porogen may be dependent on the type of porogen selected and the degree of porosity desired for the hydrogel particles. In one set of embodiments, a porogen may be present in at least one selected from the first aqueous composition and the second aqueous composition in an amount up to 2 wt %.

Additionally, surfactants can be employed in the process and when used, suitable surfactants may be incorporated in one or more of the first aqueous composition, the second aqueous composition and/or in the lipophilic composition used to prepare the injectable composition. In one embodiment, the lipophilic composition used to form the oil phase of the water-in-oil emulsion of the injectable composition comprises a surfactant.

The injectable composition of the invention may be prepared in a one-step process, which provides a simple and effective method of production. Conventional manufacturing equipment and apparatus can be used to prepare the composition, which aids in reducing production costs.

The injectable composition of embodiments described herein, which may be prepared in accordance with processes described herein, is capable of being administered to a subject for the delivery of the biologically active agent. It is suitably administered in a single injection. Advantageously, the injectable composition may be used as prepared, without the need for additional isolation, purification or formulation steps to be performed. For instance, the present invention avoids the need to isolate the hydrogel particles and to re-formulate the isolated hydrogel particles in a suitable pharmaceutically acceptable carrier or vehicle prior to their administration to a subject. However, a skilled person would appreciate that processes such as sterilisation may be carried out in relation to the injectable composition to ensure that it complies with relevant safety or regulatory requirements.

The injectable composition of embodiments described herein is of a viscosity that is suitable for administration by injection to a subject. It has been found that the injectable composition can exhibit shear thinning behaviour when shear stress is applied, such as when the composition is injected through the lumen of a needle. Shear thinning that occurs under applied shear stress can reduce the viscosity of the composition.

The release profile of a biologically active agent from the injectable composition includes a short-term (i.e. rapid) and a long-term (i.e. sustained) portion. In some embodiments, the release profile of the biologically active agent can be controlled or modulated by components of the injectable composition influencing the passage of the active agent by various mechanisms as described herein.

The short-term release profile allows a primary dose of the biologically active agent to be rapidly delivered. It is believed that the primary dose is provided by that portion of the biologically active agent that is not contained in the hydrogel particles but is instead present in the aqueous liquid of the aqueous phase of the water-in-oil emulsion. As the biologically active agent is not bound or encapsulated in the solid hydrogel particles (i.e. it is free of the hydrogel particles), the active agent in the aqueous liquid is able to be rapidly delivered to a subject in vivo.

It is believed that the delivery of a primary dose of the biologically active agent can occur when a droplet of the aqueous liquid containing the active agent separates from the dispersed aqueous phase and is transported through the continuous oil phase of the water-in-oil emulsion. The aqueous liquid droplet may be encapsulated by an oil film during its transport through the oil phase. The oil encapsulated aqueous droplet containing the biologically active agent is then delivered to the surrounding physiological environment, where the active agent contained in the droplet can be released as an initial primary dose.

This rapid delivery of a primary dose of the biologically active agent occurs immediately upon administration of the injectable composition to a subject, or shortly thereafter (i.e. within minutes of administration).

In some embodiments, release of the biologically active agent may be modulated by interactions that the biologically active agent may have with hydrogel particles in the injectable composition. For example, if the biologically active agent and hydrogel polymer matrix each carry a net charge at physiological pH, electrostatic interactions between the biologically active agent and hydrogel polymer matrix may influence the release kinetics of the active agent. Similarly, a charged coating may also interact with a charged biologically active agent electrostatically and thus influence the release of the active agent.

In one form of the injectable composition of embodiments described herein the biologically active agent in the hydrogel particles may be conjugated to the particles. Conjugation may be via covalent or non-covalent interactions. The biologically active agent may be conjugated to the crosslinked polymer matrix of the hydrogel particle and/or to a coating covering the hydrogel particle. In one embodiment, the biologically active agent is conjugated via non-covalent interactions, such as electrostatic interactions. This may occur when the biologically active agent is charged at physiological pH and the polymer matrix of the hydrogel particle and/or the coating on the hydrogel particle bears an opposite charge.

In some embodiments, the short-term release profile of the biologically active agent is linear and may be of zero order.

The delivery of the biologically active agent to the physiological environment can also be modulated by an adjuvant in the injectable composition. In embodiments where the oil phase of the water-in-oil emulsion comprises an adjuvant such as an adjuvanting oil, the oil film surrounding the aqueous droplet will also comprise the adjuvant. In such embodiments, the adjuvant in the oil film will help to modulate the release of the biologically active agent from the aqueous liquid droplet to the subject's physiological environment.

More prolonged (i.e. sustained) delivery of the biologically active agent may be achieved after delivery of the primary dose via release of that portion of the active agent, which is contained in the hydrogel particles of the injectable composition. Accordingly, the particles of hydrogel may act as a depot for the biologically active contained within. Release of quantities of the active agent from the particles over time enables the injectable composition of the invention to deliver a biologically active agent to a subject over a sustained period of time, thus providing for longevity of response.

In order to provide for sustained delivery, the biologically active agent contained within the hydrogel particles passes from the hydrogel particles into the aqueous liquid of the aqueous phase. Once in the aqueous liquid, the biologically active agent may then be delivered to a subject's physiological environment via the same oil film encapsulated aqueous droplet mechanism described above for delivery of the primary dose of active agent.

Passage of the biologically active agent from the hydrogel particles to the aqueous liquid may be assisted by a concentration gradient being established for the active agent or by differences in osmotic pressure between the hydrogel particles and the aqueous liquid, which might encourage the movement of the active agent from the hydrogel particles to the aqueous liquid.

In particular, rapid and sustained delivery of the biologically active agent to a physiological environment can be influenced by a dynamic equilibrium being established for the active agent. In that regard, it is believed that the injectable composition of the invention can provide a partition system facilitating the establishment of an equilibrium between active agent bound to or contained in the hydrogel particles and active agent free in the aqueous liquid of the dispersed aqueous phase of the water-in-oil emulsion. The partition, resulting from the binding equilibrium, provides an initial rapid release of free syneresis active agent, giving the priming dose, which in the presence of an adjuvant can trigger innate immunity responses (i.e. macrophages, dendritic cells). The bioactive species physically bound to the network chains of the hydrogel provides longer term trickle feed (i.e. sustained release) of the active agent either by re-establishment of further "free" state species re-establishing the binding equilibrium or by uptake of the microhydrogels by antigen presenting cells (APCs) by such processes as phagocytosis (if hydrogel is greater than ~1 μm), micropinocytosis (if hydrogel is less than 1 μm) or endocytosis (if hydrogel is nanoscale ~50-60 nm). Microhydrogels containing antigen can further trigger the adaptive immune system inducing the differentiation of the T cells to T helper and T killer cells resulting into production of specific antibodies (i.e., adaptive immunity).

In some embodiments, where electrostatic interactions dominate designed partition, consisting of an equilibrium between the active agent bound to the biopolymer chains of the hydrogel and the active agent free in the dispersed aqueous phase of the water-in-oil emulsion, the composition of the biopolymer can be adjusted to tailor the proportion of bioactive agent deliverable in the rapid (aqueous) and sustained (bound) delivery stages.

In some embodiments, the bioavailability profile of the biologically active agent may involve modulation of the presentation of the active agent to the in vivo environment. For example, presentation of the active agent can be modulated via the internalization of the hydrogel particles in macrophages and dendritic cells followed by the lysing of the hydrogel to release the active agent into the cytoplasm of the antigen presenting cells (APC).

Effective short term and long term release of the biologically active agent can be achieved without the need to apply an external stimulus to trigger release of the active agent from the injectable composition.

A skilled person would also appreciate that the morphology of the hydrogel particles may change after injection intramuscularly or subcutaneously. Pressure exerted by the surrounding biological tissue may result in packing of the hydrogel particles in the water-in-oil emulsion at the injection site with a small amount of emulsion liquid only surrounding and filling the spaces between hydrogel particles. This results in the filtrating out of the aqueous and oil liquids which contains the biologically active agent, to be delivered as the primary dose upon injection of the composition to a subject.

Hydrogel particles may also contract over time after injection, resulting in the expulsion of aqueous liquid contained within the particles, hence resulting in the biologically active agent being expelled from the particles and into the surrounding aqueous environment. The biologically active agent remaining contained in the hydrogel particles may be expelled from the particles at a slower rate and thus contribute to providing sustained delivery of the active agent.

Passage of the biologically active agent from the hydrogel particles to the aqueous liquid may also be modulated by a coating present on one or more of the hydrogel particles of the injectable composition. Depending on its composition and possible interactions with a biologically active agent, a coating may impede the movement the active agent from the hydrogel particles into the aqueous liquid and thus help to promote sustained release of the active agent from the injectable composition over a prolonged period of time.

In some embodiments the materials used to prepare the hydrogel particles may further assist in the sustained delivery of the biologically active agent as such materials may have adjuvanting properties and thus act as adjuvants to help modulate the passage of the active agent from the hydrogel particles to the aqueous liquid. For example, chitosan may have adjuvanting properties and hydrogel particles comprising crosslinked chitosan may be capable of influencing the release of the biologically active agent and enhance immune response.

Modulation of the release of the biologically active agent may involve an increase or a decrease in the rate of active agent delivery to the physiological environment.

As used herein, the phrase "sustained release" means that the rate of release of the agent to the subject is slower than would occur if the agent were administered to the subject directly.

In one example, an injectable composition of the present invention comprises Bm86 as an active agent and is able to provide an immune response to Bm86 over a period of at least 6 months in vivo.

In an embodiment, specific components of the injectable composition may be present in the following % wt range: polysaccharide (0.05-3%): crosslinking agent (0.05-3%): aqueous insoluble alkaline earth metal phosphate (0.0-3% subject to particle size distribution): glycosaminoglycans (GAGs) from about (0.0-3%).

The injectable composition of embodiments described herein may have a low proportion of solids in the water-in-oil emulsion.

One advantage of the injectable composition of the invention is that it enables fewer injections to be administered to a subject. For example, for conditions that would normally require daily injections under current conventional regimes, the present invention may allow the substantially the same physiological effects and benefits to be achieved with weekly injections.

Additionally, regimes requiring an initial injection to be followed up by one or more subsequent injections or booster injections may be simplified, as the extended bioavailability provided by the injectable composition of the present invention means that an effective physiological benefits may be achieved with a single injection, thus obviating the need for subsequent or booster injections to be administered. For instance, it has been found that the injectable composition of the present invention is able to induce effective protective immunity (i.e. antibody levels) in a subject following a single injection without the need for subsequent follow up single or multiple injections. Furthermore, an effective level of immunity was maintained over a number of weeks. In some embodiments, an effective level of immunity could be maintained over a period of several months, and in one embodiment, immunity may be maintained for more than a year.

The ability to reduce the number of injections may therefore afford increased convenience to a subject receiving the injections, as well as cost savings to the manufacturer and the consumer.

In use, the injectable composition may be contained in a syringe chamber and injected through the lumen of a needle for administration to a subject. For example, the injectable composition may be administered via a gauge 23 needle.

A further advantage of the injectable composition of the invention that the composition can be tailored to contain different proportions of hydrogel particles and aqueous liquid in the aqueous phase of the composition. In this manner, the invention can control the proportion of biologically active agent contained in the hydrogel particles and in the aqueous liquid respectively. This in turn could influence the amount of active agent that would available for rapid (short term) and sustained (long term) delivery.

Further control over the release of the biologically active agent can also be achieved through the appropriate selection of material used to form the hydrogel particles, as well as through the formation of a coating on the hydrogel particles. As discussed above, the polymer in the hydrogel particles and a coating on the hydrogel particles each have the potential to interact with a selected biologically active agent and thus may modulate the release of that biologically active agent from the hydrogel particles into the aqueous liquid component of the aqueous phase of the injectable composition.

In still a further aspect the invention provides a method of delivering a biologically active agent to a subject comprising the step of administering an injectable composition as described herein to the subject by injection.

The injection may be subcutaneous, intramuscular or intraperitoneal. Preferably, administration is via subcutaneous injection.

The injectable composition of the invention has application in the administration of a biologically active agent, such as a pharmaceutical drug or vaccine.

The injectable composition of the invention may be administered to a subject in order to treat or prevent a disease or condition. As used herein the terms "treating" and "preventing" mean any treatment of prevention of a disease or condition in a subject. "Treatment" and "prevention" includes: (a) controlling or inhibiting the disease or condition, i.e., arresting its development or progression; or (b) relieving or ameliorating the symptoms of the disease or condition, i.e., cause regression of the symptoms of the disease or condition. The effect may be prophylactic or therapeutic in terms of a partial or complete cure of the disease or condition.

"Disease" as used herein is a general term used to refer to any departure from health in which a subject suffers and which can be treated or prevented using a microhydrogel-depot, which provides prolonged release of an active agent. A "condition" refers to an abnormal function of part of the body of a subject and which can be treated or prevented using a microhydrogel-depot which provides prolonged release of an active agent.

In use, the injectable composition of the invention provides rapid and sustained release of a biologically active agent to a subject in vivo. Accordingly, upon administration to a subject, the injectable composition rapidly provides an initial primary dose of the biologically active agent to the subject followed by more sustained (i.e. trickle) dosing of the active agent over a longer period of time.

In another aspect the present invention provides a method of treating or preventing a disease or disorder in a subject comprising the step administering an injectable composition of one or more embodiments as described herein to the subject by injection.

In some embodiments, the disease or disorder is a microorganism infection and the injectable composition of the invention may be used to treat or prevent the microorganism infection. Microorganisms may include bacteria, fungi and viruses.

In some embodiments, the disease or disorder is a viral infection and the injectable composition of the invention may be used to treat or prevent the viral infection.

In some embodiments, the disease or disorder is a parasite infestation and the injectable composition of the invention may be used to treat, control or prevent the infestation. For example, the injectable composition may be used to control a tick infestation.

In other embodiments, the injectable composition may be used to inhibit a normal condition, (e.g. reproductive condition) that is arrested in progress or development.

The subject in which a disease or condition is to be treated or prevented may be a human or an animal of economical importance and/or social importance to humans, for instance, carnivores other than humans (such as cats and dogs), swine (pigs, hogs, and wild boars), ruminants (such as cattle, oxen, sheep, giraffes, deer, goats, bison, and camels), horses, and birds including those kinds of birds that are endangered, kept in zoos, and fowl, and more particularly domesticated fowl, e.g., poultry, such as turkeys, chickens, ducks, geese, guinea fowl, and the like, as they are also of economical importance to humans. The term does not denote a particular age. Thus, both adult and newborn subjects are intended to be covered.

In particular embodiments, the subject is a livestock animal, such as cattle, sheep or pigs. In such embodiments, the injectable composition may be considered to be a veterinary composition, and the biologically active agent contained in the composition is selected for the treatment or prevention of a disease or condition in the livestock animal.

The present invention also provides use of an injectable composition of one or more embodiments as described herein in the manufacture of a medicament for the treatment or prevention of a disease or disorder in a subject.

In some embodiments of the method or use described herein, the biologically active agent is an antigen. In particular, the antigen may be Bm86 or TSOL18.

In other embodiments of the method or use described herein, the biologically active agent is a hormone. In particular, the hormone may be somatotropin or luteinizing hormone-release hormone (LHRH).

As used in the subject specification, the singular forms "a", "an" and "the" include plural aspects unless the context clearly dictates otherwise. Thus, for example, reference to a "virus" includes a single viral particle as well as two or more viral particles, "a gene" includes a single gene or two or more genes. Reference to "the invention" includes single or multiple aspects of the invention.

Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

The invention will now be described with reference to the following examples. However, it is to be understood that the examples are provided by way of illustration of the invention and that they are in no way limiting to the scope of the invention.

EXAMPLES

Materials and Methods

Low molecular weight chitosan having Mw of 164 kDa, 75-85% degree of deacetylation and a viscosity of 0.026 Pa·s for a 1 wt % solution in 1% acetic acid was obtained from Sigma-Aldrich. Hydroxyapatite (HAp) (Type I, Suspension in 0.001 M phosphate buffer, pH 6.8; approx. 25% solids) was obtained from Sigma-Aldrich. This suspension was dispersed in the chitosan solution using a high shear mixer (MICCRA and DS-8/P stator rotor—Stator; spike head8 mm) at 20000 rpm for 5 min to produce 1 mg HAp/mL. Sodium tripolyphosphate pentabasic (TPP) (technical grade, 85%) and chondroitin sulphate A sodium salt (ChS) (from bovine trachea lyophilized powder, BioReagent) were obtained from Sigma-Aldrich. The adjuvant Montanide ISA61 VG was from Seppic SA (Paris La Defense, France). Sesame oil, Tween 80, and medium viscosity sodium alginate (brown algae) were from Sigma-Aldrich. Anti-cattle tick Bm86 antigen (Bm86), anti-tapeworm TSOL18 antigen (TSOL18) and porcine somatotropin (pST) were produced and characterised as reported in the following literature: (1) Bm86: Willadsen, P. et al, The Journal of Immunology, 1989. 143(4): p. 1346-1351; (2) TSOL18: Gauci, C. and M. W. Lightowlers, Molecular and Biochemical Parasitology, 2003. 127(2): p. 193-198; (3) pST: Ouyang, J. et al, Protein Expression and Purification, 2003. 32(1): p. 28-34.

Injectable Vaccine Compositions with Bm86 Antigen

Three different component solutions were prepared, each having a range of concentrations:

Part [A]: Bm86 (0 μg, 50 μg, 100 μg or 200 μg) dissolved in an aqueous solution of 2% chitosan or 2% chitosan with 1 mg hydroxyapatite (HAp)/mL Part [B]: tripolyphosphate (TPP) solution (0.04M, 0.08M, 0.16M or 0.32M) or TPP solution (0.04M, 0.08M, 0.16M or 0.32M) with 1% chondroitin sulphate (ChS)

Part [C]: Montanide ISA61 VG

To prepare the vaccine composition, a desired quantity of solution [A] was initially emulsified with a quantity of solution [C] using MICCRA high shear emulsifier at 20,000 rpm rate for 2-3 min. A desired quantity of solution [B] was then added dropwise under constant shearing at the same rate as before (2-3 min) to form injectable composition. The consistency of the emulsion was examined by withdrawing in a syringe using a 23 gauge needle to assess the injectability of the composition.

Examples 1 to 6

The Effect of Crosslinker (TPP) Solution Volume

In these examples, 1 mL of [A] containing HAp was emulsified in 2 mL of [C] then various volumes of [B] with 0.08 M TPP containing ChS was added dropwise under continuous shearing. The volumes of [B] were 0.5 mL, 1 mL, 1.5 mL, 2 mL, 2.5 mL, and 3 mL. The consistency of the emulsion was tested using the syringe and a 23 gauge needle after 10-15 min rest. The hydrogel particle formation was confirmed by centrifuging the emulsion at 14000 g for 5 min and observation of the hydrogel particles, aqueous phase and oil phase. The results are shown in Table 1. In unstable compositions, the emulsion collapsed, or inverted over time to an oil-in-water emulsion.

TABLE 1

Compositions prepared with 0.08M TPP in 1% ChS as solution [B]

| Example | Vol [A] (ml) | Vol [B] (ml) | Vol [C] (ml) | Comments |
|---|---|---|---|---|
| 1 | 1 | 0.5 | 2 | Stable emulsion |
| 2 | 1 | 1 | 2 | Stable emulsion |
| 3 | 1 | 1.5 | 2 | Stable emulsion |
| 4 | 1 | 2 | 2 | Stable emulsion |
| 5 | 1 | 2.5 | 2 | Unstable |
| 6 | 1 | 3 | 2 | Unstable |

Examples 7 to 24

The Effect of the Crosslinker (TPP) Concentration

In these examples, 1 mL of [A] containing HAp was emulsified in 2 mL of [C] then various volumes of [B] with 0.04 M, 0.16 M or 0.32 M TPP containing ChS were added dropwise under continuous shearing. Various volumes of [B] (0.5 mL, 1 mL, 1.5 mL, 2 mL, 2.5 mL or 3 mL) were then gradually added and the consistency of the emulsion was tested using the syringe and 23 gauge needle after 10-15 min rest. The hydrogel particle formation was confirmed as above. The results are shown in Tables 2, 3 and 4.

TABLE 2

Compositions prepared with 0.04M TPP in 1% ChS as solution [B]

| Example | Vol [A] (ml) | Vol [B] (ml) | Vol [C] (ml) | Comments |
|---|---|---|---|---|
| 7 | 1 | 0.5 | 2 | Stable emulsion |
| 8 | 1 | 1 | 2 | Stable emulsion |
| 9 | 1 | 1.5 | 2 | Stable emulsion |
| 10 | 1 | 2 | 2 | Stable emulsion |
| 11 | 1 | 2.5 | 2 | Unstable |
| 12 | 1 | 3 | 2 | Unstable |

TABLE 3

Compositions prepared with 0.16M TPP in 1% ChS as solution [B]

| Example | Vol [A] (ml) | Vol [B] (ml) | Vol [C] (ml) | Comments |
|---|---|---|---|---|
| 13 | 1 | 0.5 | 2 | Stable emulsion |
| 14 | 1 | 1 | 2 | Stable emulsion |
| 15 | 1 | 1.5 | 2 | Stable emulsion |
| 16 | 1 | 2 | 2 | Stable emulsion |
| 17 | 1 | 2.5 | 2 | Unstable |
| 18 | 1 | 3 | 2 | Unstable |

TABLE 4

Compositions prepared with 0.32M TPP in 1% ChS as solution [B]

| Example | Vol [A] (ml) | Vol [B] (ml) | Vol [C] (ml) | Comments |
|---|---|---|---|---|
| 19 | 1 | 0.5 | 2 | Stable emulsion |
| 20 | 1 | 1 | 2 | Stable emulsion |
| 21 | 1 | 1.5 | 2 | Stable emulsion |
| 22 | 1 | 2 | 2 | Stable emulsion |
| 23 | 1 | 2.5 | 2 | Unstable |
| 24 | 1 | 3 | 2 | Unstable |

Examples 25 to 32

The Effect of Polymer (Chitosan) Solution Volume

In these examples, 2 mL of [A] containing HAp was emulsified in 2 mL of [C] then [B] (0.16 M or 0.32 M TPP) containing ChS was added dropwise to the emulsion under continuous shearing. Various volumes of [B] (0.5 mL, 1 mL, 1.5 mL, and 2 mL) were employed and the injectability and consistency of emulsion was tested. The results are shown in Tables 5 and 6.

TABLE 5

Compositions prepared with 0.16M TPP in 1% ChS as solution [B]

| Example | Vol [A] (ml) | Vol [B] (ml) | Vol [C] (ml) | Comments |
|---|---|---|---|---|
| 25 | 2 | 0.5 | 2 | Stable emulsion |
| 26 | 2 | 1 | 2 | Stable emulsion |
| 27 | 2 | 1.5 | 2 | Unstable |
| 28 | 2 | 2 | 2 | Unstable |

TABLE 6

Compositions prepared with 0.32M TPP in 1% ChS as solution [B]

| Example | Vol [A] (ml) | Vol [B] (ml) | Vol [C] (ml) | Comments |
|---|---|---|---|---|
| 29 | 2 | 0.5 | 2 | Stable emulsion |
| 30 | 2 | 1 | 2 | Stable emulsion |
| 31 | 2 | 1.5 | 2 | Unstable |
| 32 | 2 | 2 | 2 | Unstable |

Examples 33 to 44

The Emulsification Order

Vaccine compositions containing Bm86 were produced using the following component solutions:

Part [A2]: An aqueous solution of 2% chitosan with 1 mg hydroxyapatite (HAp)/mL

Part [B2]: Bm86 (0 μg, 50 μg, 100 μg or 200 μg) dissolved in an aqueous TPP solution (0.16M or 0.32M) with 1% chondroitin sulphate (ChS)

Part [C]: Montanide ISA61 VG

A quantity of component solution [B2] was emulsified in oil [C] first, then the chitosan component solution [A2] was added to produce the final microhydrogel in water-in-oil emulsion. In these examples Bm86 was incorporated in the ChS-TPP component solution [B2].

In these examples, 1 mL of [B2] (with 0.16 or 0.32 M TPP) was emulsified with 2 mL of [C] then various volumes of [A2] (0.5 mL, 1 mL, 1.5 mL, 2 mL, 2.5 mL or 3 mL) were added dropwise under continuous shearing. The results are shown in Tables 7 and 8. Compositions forming a mousse were found to be uninjectable using 23 G×33 mm syringe needle.

TABLE 7

Compositions prepared with 0.16M TPP in 1% ChS as solution [B2]

| Example | Vol [A2] (ml) | Vol [B2] (ml) | Vol [C] (ml) | Comments |
|---|---|---|---|---|
| 33 | 0.5 | 1 | 2 | Stable emulsion |
| 34 | 1 | 1 | 2 | Stable emulsion |
| 35 | 1.5 | 1 | 2 | Stable emulsion |
| 36 | 2 | 1 | 2 | Stable emulsion |
| 37 | 2.5 | 1 | 2 | Unstable - mousse |
| 38 | 3 | 1 | 2 | Unstable - mousse |

TABLE 8

Compositions prepared with 0.32M TPP in 1% ChS as solution [B2]

| Example | Vol [A2] (ml) | Vol [B2] (ml) | Vol [C] (ml) | Comments |
|---|---|---|---|---|
| 39 | 0.5 | 1 | 2 | Stable emulsion |
| 40 | 1 | 1 | 2 | Stable emulsion |
| 41 | 1.5 | 1 | 2 | Stable emulsion |
| 42 | 2 | 1 | 2 | Stable emulsion |
| 43 | 2.5 | 1 | 2 | Unstable - mousse |
| 44 | 3 | 1 | 2 | Unstable - mousse |

Example 45

Injectable Vaccine Composition with Bm86 Antigen

An injectable vaccine composition containing Bm86 antigen was prepared from the following component solutions as follows:

Part [C]: Montanide ISA61 VG

Part [D]: The required dose of Bm86 (for example 400 μg Bm86/mL) dissolved in an aqueous solution of 0.32 M TPP with 1% chondroitin sulphate (ChS)

Part [E]: 2% chitosan solution with 1 mg hydroxyapatite (HAp)/mL

A quantity (1 mL) of solution [D] was emulsified in 2.4 mL of Montanide ISA61 VG oil [C] using high shear (20,000 rpm, 2 min). To this emulsion, 3.6 mL of solution [E] was added drop wise under the same shear rate produced a stable injectable water-in-oil emulsion containing cross-linked chitosan hydrogel microparticles.

Example 46

Injectable Composition with Somatotropin

Three different component solutions were prepared:

Part [F]: Alginate solution in water (1 or 2% alginate) with porcine somatotropin (pST) (300, 1000 or 3000 μg/mL) as peptide hormone active agent Part [G]: Calcium chloride solution in water (2.8% or 5.6%) as the crosslinker Part [H]: Tween 80 in sesame oil (50 mg in 1 mL)

A quantity (1 mL) of solution [F] was emulsified in 2 mL of [H] using high shear (20,000 rpm, 2 min). To this emulsion, 0.5 mL of solution [G] was added drop wise under the same shear rate. A stable and injectable water-in-oil emulsion containing crosslinked alginate hydrogel particles was produced with a lipophilic composition having a 50 mg Tween 80/mL sesame oil concentration.

Example 47

Injectable Composition with Somatotropin

In this example an aqueous sodium alginate composition and a lipophilic sesame oil composition were prepared as in [F] and [H] in Example 46 and an aqueous chitosan composition was prepared as the crosslinker for the negatively charged alginate as follows:

Part [I]: 2% Chitosan solution in 1% acetic acid in water

A quantity (1 mL) of solution [F] was emulsified in 2 mL of [H] using high shear (20,000 rpm, 2 min). To this emulsion, 1 mL of solution [I] was added drop wise under the same shear rate which produced a stable and injectable water-in-oil emulsion comprising hydrogel particles formed with alginate crosslinked with chitosan.

Example 48

Model Bulk Hydrogel Composition with Somatotropin

Three different component solutions were prepared, each having a range of concentrations:

Part [J]: Alginate solution in water (0.5, 1 or 2% alginate) with porcine somatotropin (pST) (500, 1000 or 3000 μg/mL) as peptide hormone active agent Part [K]: Calcium chloride solution in water (0.3, 0.7, 1.4 or 2.8%) as the crosslinker A quantity (1 mL) of solution [J] was crosslinked using 1 mL of solution [K] to afford pST loaded bulk hydrogel. The initial syneresis (12 hours) release of pST from the model bulk hydrogel is given in FIG. 8.

Example 49

Model Bulk Hydrogel Composition with Somatotropin

Different component solutions were prepared:

Part [L]: Alginate solution in water (1% alginate) with porcine somatotropin (pST) (500, 1000 or 3000 μg/mL) as peptide hormone active agent and PEG (35 kDa) porogen (0, 0.5, 1, or 2 wt % PEG)

Part [K]: Calcium chloride solution in water (0.3, 0.7, 1.4 or 2.8%) as the crosslinker A quantity (1 mL) of solution [L] was crosslinked using 1 mL of solution [K] to afford pST loaded bulk hydrogel. After the removal of the syneresis initial liquid long term release of pST (4 weeks) from the model bulk hydrogel was monitored by refreshing the hydrogel surrounding liquid using PBS solution every 48 hours and measuring the pST in PBS. The release profile is given in FIG. 9.

Animal Trials

Dorper sheep were used as models to evaluate the immunological performance of the Bm86-hydrogel in oil system in a study under approval of The University of Queensland Animal Ethics Committee. Sheep were female, 5-7 months old, and 12-16 kg weight at the start of the trial. The sheep trial consisted of two groups with four animals per group. The first group was a positive control inoculated subcutaneously with two injections of a comparative formulation representing a conventional anti-tick formulation, which was given as an initial primary dose followed by a booster dose after 4 weeks. Each dose contained an emulsion of aqueous 50 μg Bm86 in 1.2 mL Montanide ISA61 VG adjuvanting oil. The second group was inoculated with an injectable Bm86 vaccine composition prepared in accordance with the procedure of Example 45. In brief, one dose of microgel in emulsion formulation prepared by dissolving 200 ug Bm86 and 50 mg ChS in 0.5 mL of 0.32 M TPP and emulsified in 1.2 mL Montanide ISA60 VG, then 1.8 mL of (2% chitosan—1 mg HAp/mL) was emulsified in this initial primary emulsion to give 200 ug Bm86 and 3.5 mL per dose. A single dose of the Bm86 composition was administered by subcutaneous injection. Anti-Bm86 titres were measured as IgG, and determined by ELISA assay every two weeks. The trial results are shown in FIGS. 2 and 12 (in FIG. 12, Ab units relative to negative control group at 1/25600 dilution).

The trial results show that:

The Bm86 vaccine composition of the invention produces protective immunity (antibody (Ab) levels) in a single vaccine injection not requiring follow up single or multiple booster injections.

With the selected vaccine antigen (Bm86) the antibody titre levels at day 150 of the trial were higher than the comparative formulation, which was administered using 2 injections.

At up to 150 days of the trial, the vaccine composition established a period of anti-tick immunity not achieved by the comparative formulation. The antibody response continued at protective levels up to one year after a single injection.

The immune response with the vaccine composition as described in Example 45 is higher than the comparative formulation, which produces protective levels only after day 28.

Over a trial duration of more than 400 days, antibody titre levels remained significantly higher than the comparative formulation, demonstrating a longer term immune response following a single injection of the vaccine composition.

In Vitro Release Results

Release of Biologically Active Agent from a Model Bulk Chitosan Hydrogel (Primer Dose)

The ability to achieve an initial release of Bm86 from a chitosan hydrogel was tested by monitoring the concentration of Bm86 in the aqueous phase immediately after mixing the polymer and crosslinker solutions and hydrogel formation.

Figure 1:
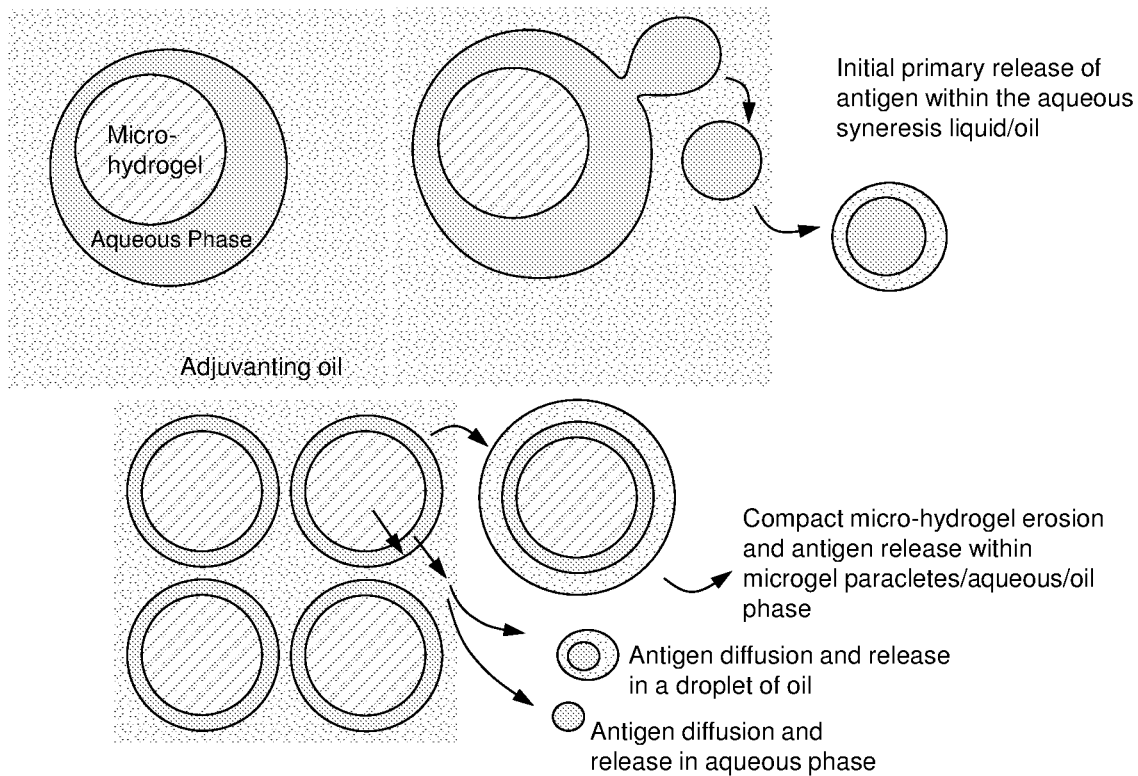
Figure 2:
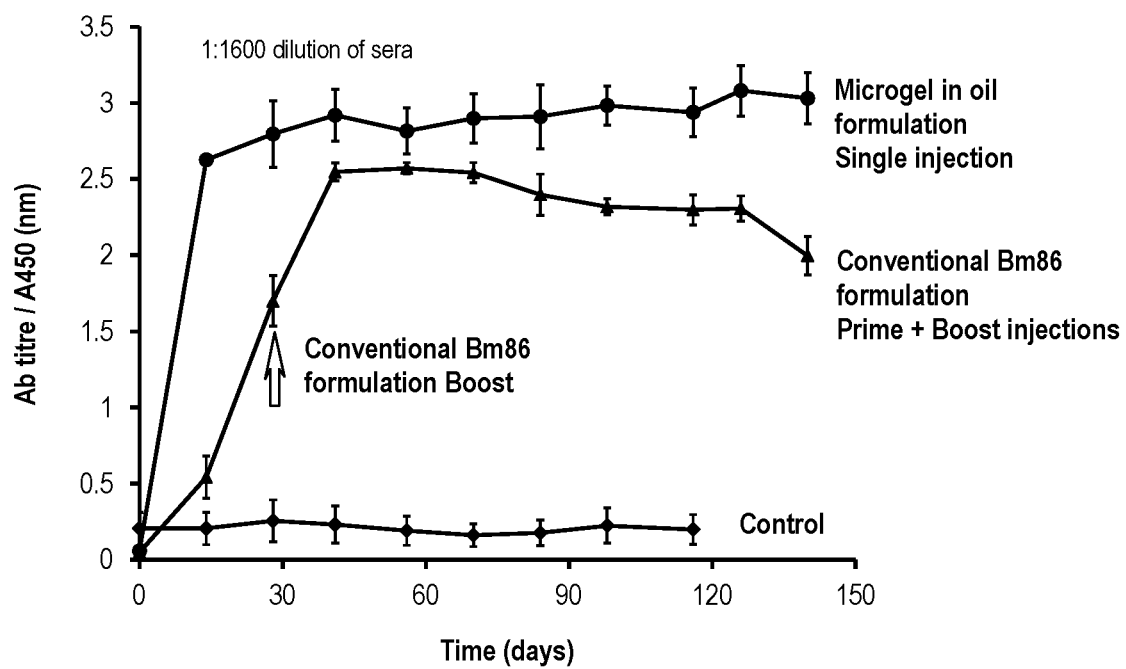
Figure 3:
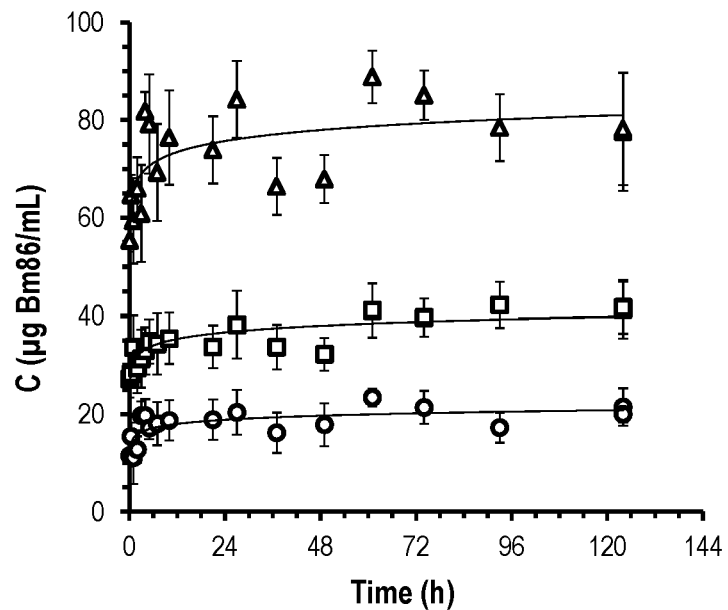
Figure 3:
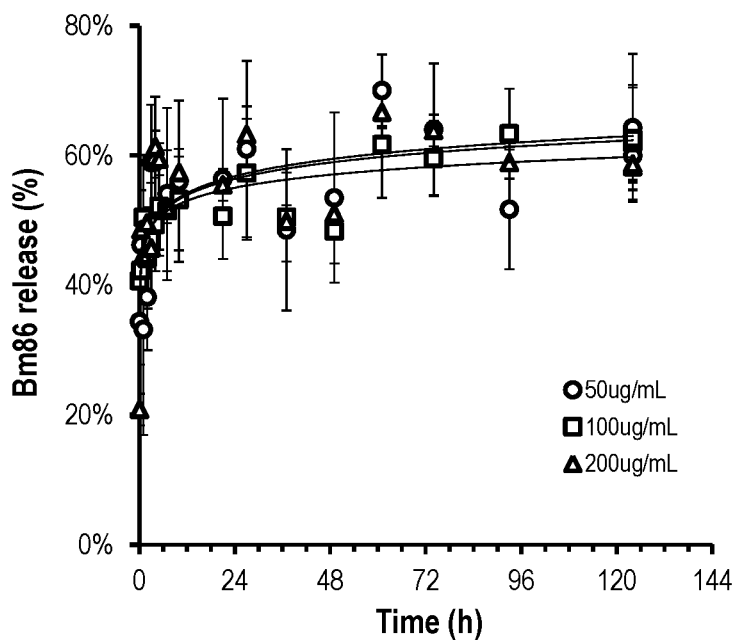

FIG. 3 shows results from a study to assess the in vitro release of Bm86 from a model bulk chitosan hydrogel over a period of 144 hours. The bulk hydrogel is composed by mixing of 2% chitosan-HAp (1 mg/mL) solution and 0.08 M TPP-ChS (1%) solution, with different initial loading concentrations of Bm86. As seen in FIG. 3(A), the concentration of Bm86 released from the hydrogel particles into the surrounding aqueous liquid remains constant for different samples containing Bm86 concentrations of 50, 100, and 200 μg/mL in solution, giving a relative initial release of ~55-60% of the Bm86 into the aqueous liquid phase, which is available as a primary dose (FIG. 3(B)).

The Effect of Crosslinking on Long Term Release Rate

The binding coefficient of Bm86 to hydrogel is mainly dependant on the electrostatic interaction between the protein due to its isoelectric point (pI) and the polymer chains electrostatic charge in the hydrogel. This results in an equilibrium between Bm86 free in the syneresis liquid and bound to the hydrogel in the initial formation stage. This is a dynamic equilibrium, so when the free Bm86 is removed and the media is refreshed, bound Bm86 tends to be released from the hydrogel to establish a new equilibrium via a transport process. Here we studied the long term release of Bm86 from a chitosan model hydrogel at various crosslinking densities and Bm86 loading concentrations by refreshing the hydrogel aqueous environment with PBS weekly. This is a simulation of the in vivo environment where intercellular fluid is continuously refreshed.

Figure 4:
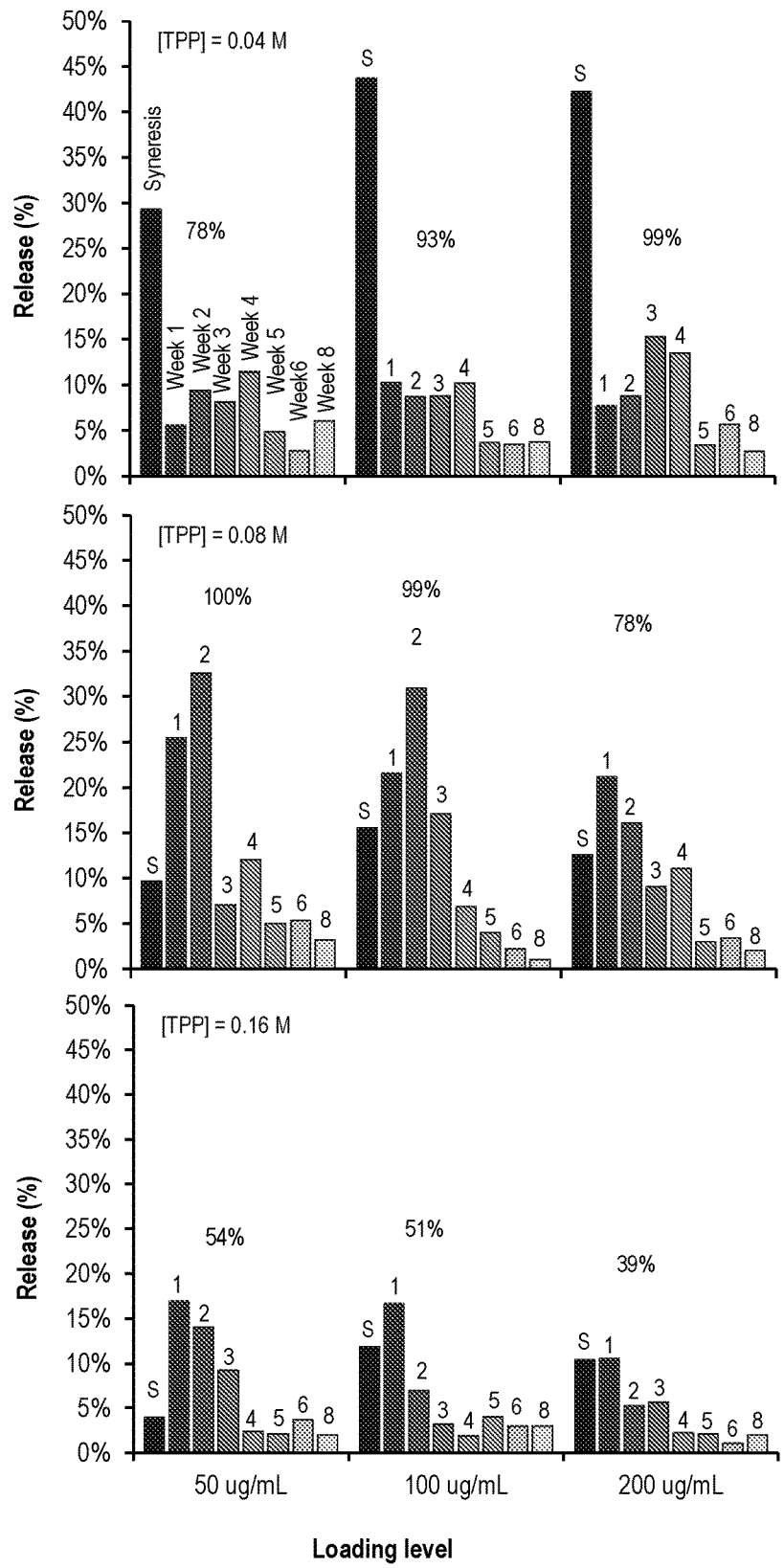

The release rate of Bm86 from a bulk chitosan hydrogel prepared with different polymer crosslinking density (0.04 M, 0.08 M or 0.16 M TPP concentrations) was measured over an 8 week period. In these examples, model bulk hydrogels were formed by mixing equal volumes of solutions containing (a) 2% chitosan with 1 mg HAp/mL and various concentrations of Bm86, and (b) 1% ChS with various concentrations of the crosslinker TPP (0.04M, 0.08M or 0.16M). The amount of Bm86 detected in the initial sample (syneresis release) gave the initial amount of Bm86 that is rapidly released by the composition as a primary dose. Then release media, i.e. PBS, was replaced with fresh solution every week. Subsequent samples collected weekly gave a progressive release profile. The results are shown in FIG. 4. As seen in FIG. 4, the crosslinking density of the hydrogel can influence both the concentration of Bm86 released in the primary dose as well as the longer term sustained release. Additionally, the total amount of Bm86 released over the cumulative 8 week period (shown as a percentage) indicates that a significant proportion of Bm86 is released over the sustained release phase. At higher crosslinking density, where [TPP]=0.16 M is used, a significant portion of the Bm86 antigen remains entrapped in the hydrogel at the end of the 8 week period.

The Effect Protein Isoelectric Point on Loading and Initial Syneresis Release

Figure 5:
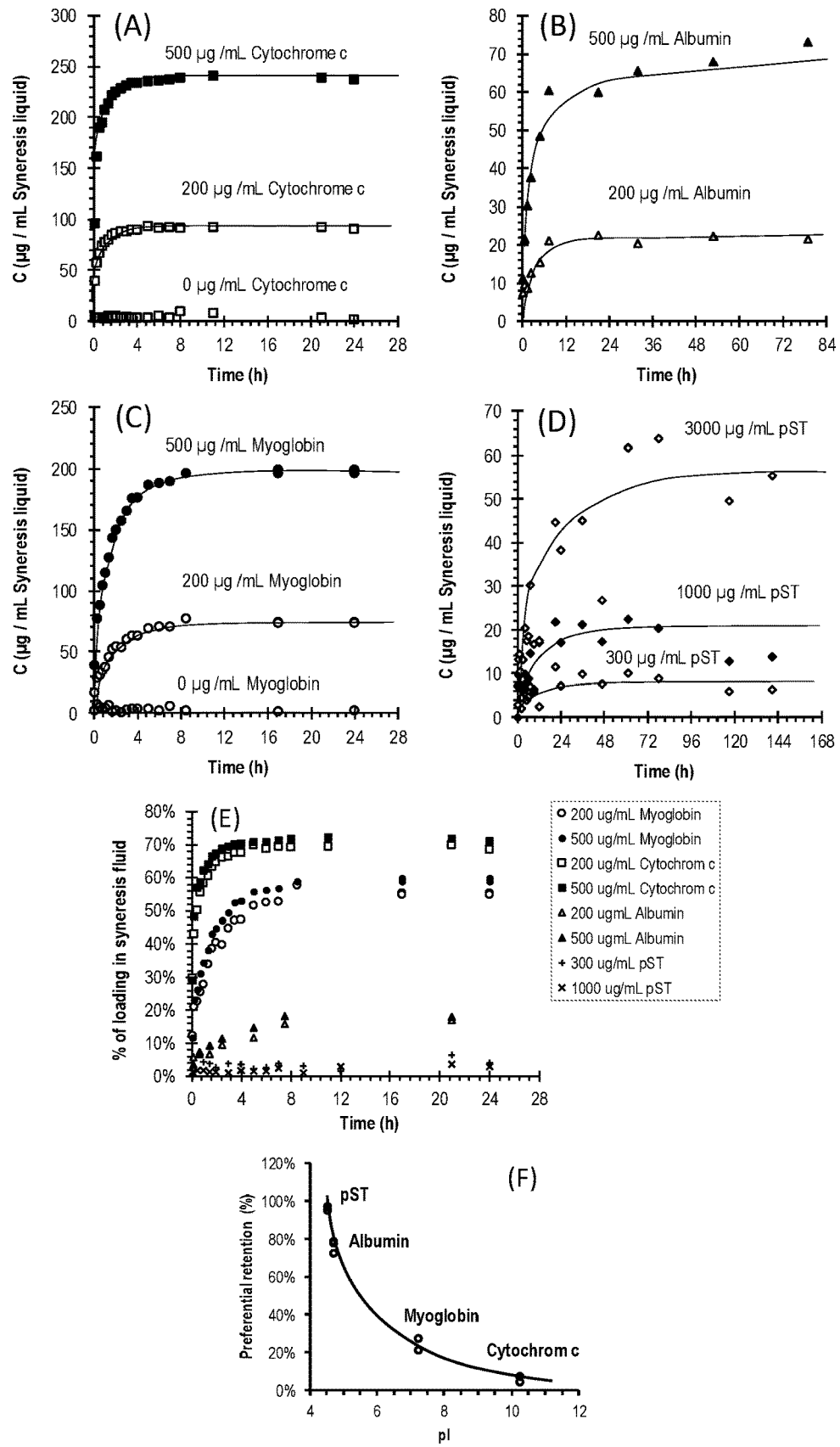

The effect of protein isoelectric point on release rate during the initial rapid release (syneresis) phase was investigated using a range of model proteins. In these examples, model bulk hydrogels were formed by mixing equal volumes of solutions containing (a) 2% chitosan with 1 mg HAp/mL and various concentrations of different proteins, and (b) 1% ChS with 0.8 M TPP. FIG. 5 gives the release rates for the proteins cytochrome C, myoglobin, albumin and the hormone pST from a bulk hydrogel formed with chitosan crosslinked with 0.08 M TPP at various model protein loading levels and expressed as concentration in the syneresis liquid (A-D) and percentage of the initial loading (E), and the relationship between the syneresis release and the isoelectric point of the loaded protein (F).

Additionally, FIG. 17 shows the partition of proteins between the bound to the hydrogel state and free in the syneresis liquid state. Bm86, pST, and albumin were used to illustrate this process at syneresis equilibrium in hydrogel formed by mixing a 2% chitosan—1 mg HAp/mL constituent with the 0.08 M TPP in 1% chondroitin sulphate crosslinking constituent. Proteins were incorporated in the chitosan containing constituent. This shows:

This equilibrium is mainly a function of the protein isoelectric point (pI), that is, the binding of the protein to the hydrogel is mainly due to electrostatic interactions.

The protein partition in the concentration ranges studied here gave a constant coefficients value which means that the protein concentrations used here are much lower than the binding capacity of the hydrogel.

Hydrogel Microparticles in a Water-in-Oil Emulsion

Figure 6:
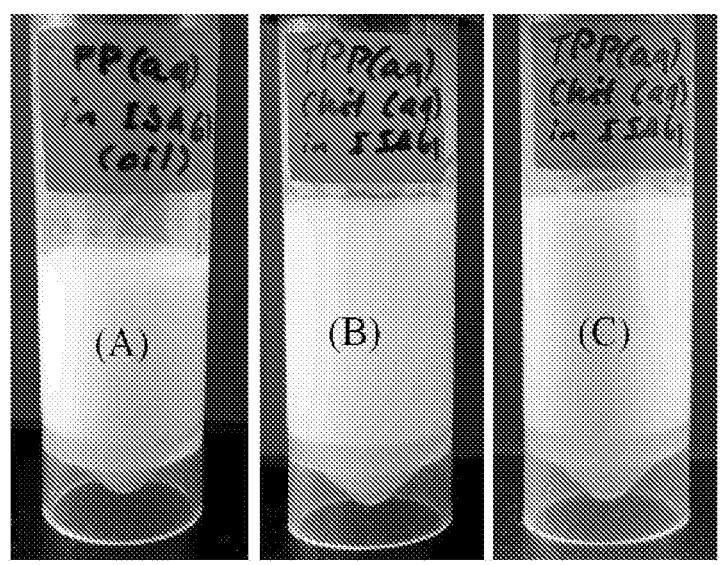

An initial water-in-oil emulsion formed with an aqueous solution of tripolyphosphate in adjuvant oil is shown in FIG. 6(A). On addition of a chitosan containing solution, crosslinked hydrogel microparticles formed within water droplets in the water-in-oil emulsion (FIG. 6(B)). The hydrogel containing water-in-oil emulsion remained stable for 5 months at 4° C., with no phase separation evident (FIG. 6(C)).

Figure 7:
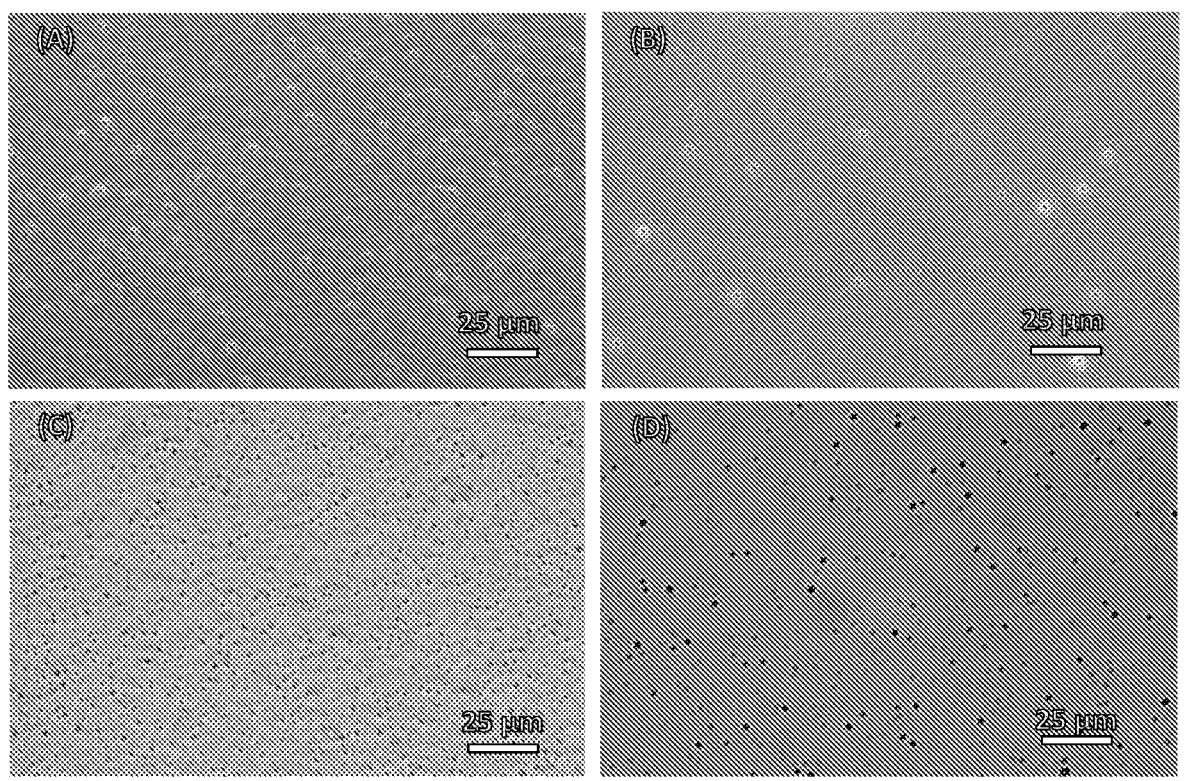
FIG. 7 shows micrographs of: (A) and (B) an injectable composition of embodiments of the invention comprising hydrogel particles, (C) an injectable composition of an embodiment of the invention after storage at 4° C. for 5 months indicating the stability of the composition, and (D) the hydrogel particles after removal of the aqueous phase from the composition by evaporation.

A composition containing hydrogel microparticles formed with chitosan (2%), HAp (1 mg/mL), TPP (0.32 M) and ChS (1%)) in a water-in-oil emulsion with Montanide ISA61 as the oil phase was analysed by optical microscopy. Results are shown in FIG. 7. As seen in FIGS. 7(A) and 7(B), the hydrogel particles in the water-in-oil emulsion are contained in aqueous droplets. In this sample, the aqueous droplets were determined to be approximately 1 to 4 μm in diameter. FIG. 7(C) shows the emulsion after storage for 5 months at 4° C. The aqueous phase was then removed from the emulsion by solvent evaporation, to give hydrogel particles of approximately 1 to 2 μm only dispersed in a continuous oil phase (FIG. 7(D)).

Release of Biologically Active Agent from Model Bulk Alginate Hydrogel (Primer Dose)

Figure 8:
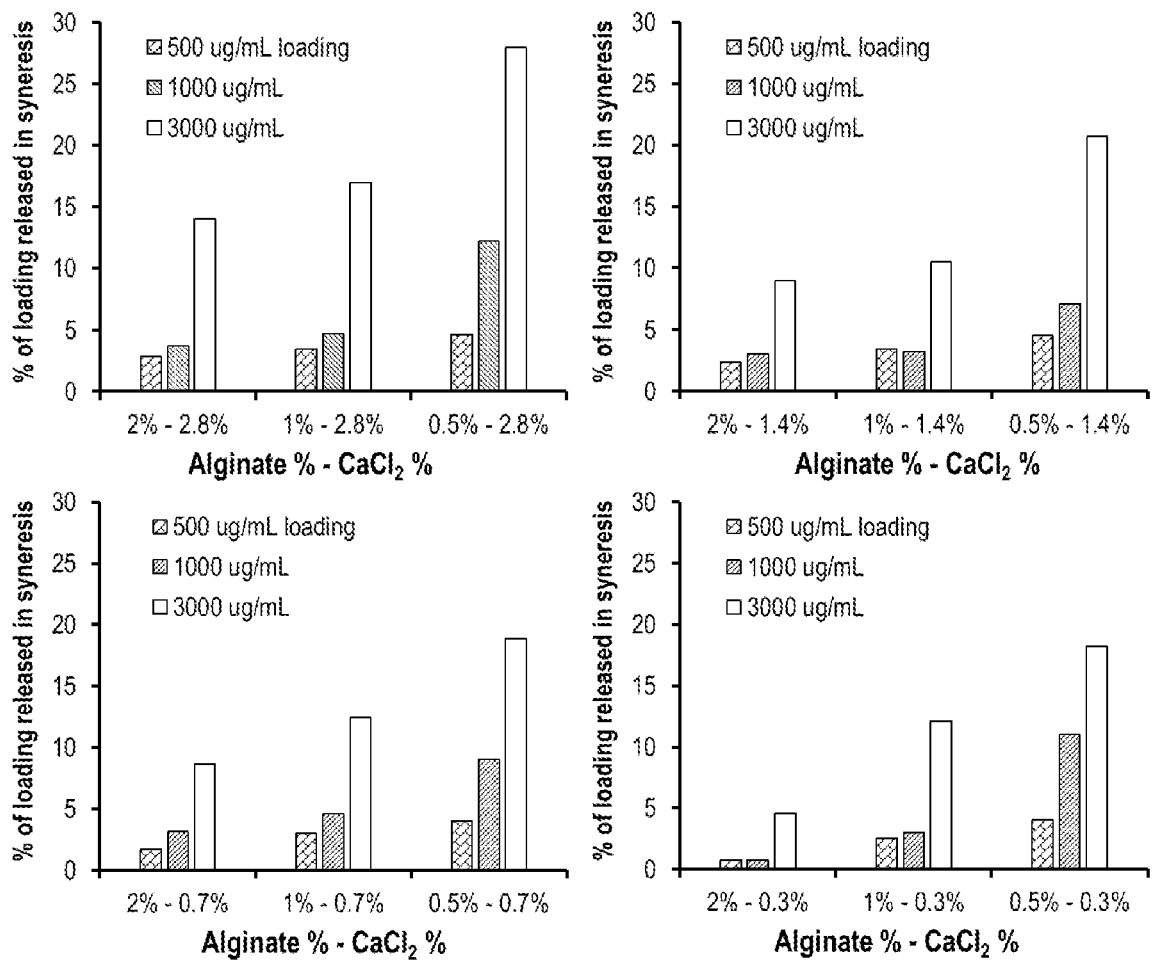
FIG. 8 is a graph showing the syneresis release of porcine somatotropin (pST) after a 12 hour period from samples of model bulk alginate—$Ca^{2+}$ hydrogels with various crosslinking ($Ca^{2+}$) densities and pST loading levels, expressed as a percentage of initial pST loading.

The release rate of porcine somatotropin (pST) from samples of bulk alginate hydrogel prepared in accordance with Example 48 was measured over 28 day period. The different hydrogel samples had different concentrations of alginate (varying from 0.5% to 2%), different crosslinking density (0.3, 0.7, 1.4 or 2.8% $CaCl_2$ concentrations) and different initial loads of pST (varying from 500 to 30000 μg/ml). The amount of pST detected in the initial sample (syneresis release) during the initial 12 hour period gave the amount of pST that is rapidly released by the composition as a primary dose. The resulting syneresis release given as a percentage of initial pST loading is shown in FIG. 8. As can be seen in FIG. 8 the syneresis release as a percentage of the pST loading increased with increasing loading level and crosslinking degree and decreased with increasing alginate concentration. This provides variations in the syneresis release between 1-28% of the pST loading, representing control of the primary injection dose in the formulation.

Figure 9:
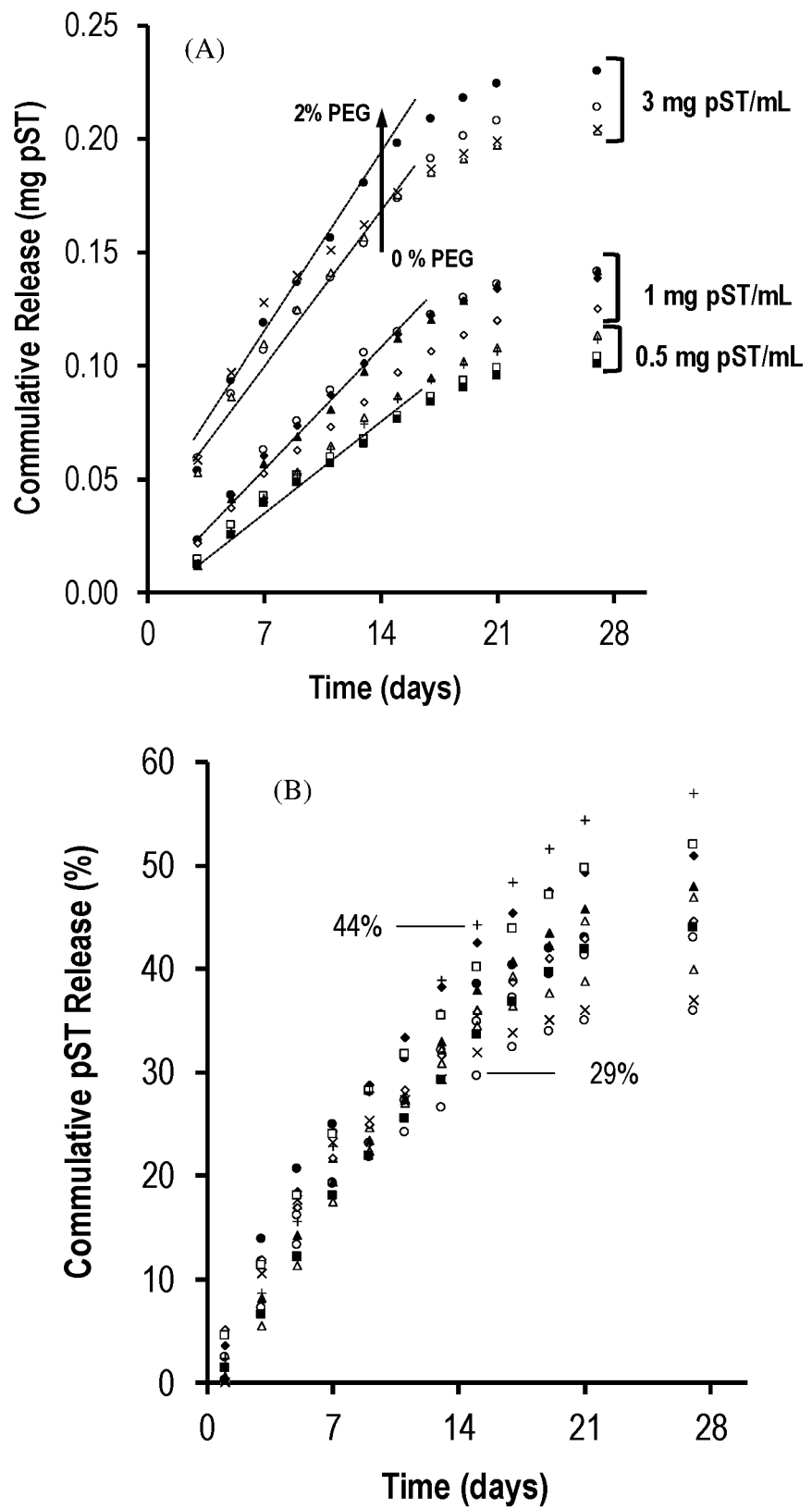
FIG. 9 is a graph showing the release of porcine somatotropin (pST) over a 28 day period from samples of model bulk alginate-$Ca^{2+}$ hydrogels formed with various amounts of PEG porogen and having various pST loading levels, expressed as (A) quantitative release, and (B) release as percentage of the total pST loading.

Longer Term Release of Biologically Active Agent from Model Bulk Alginate Hydrogel Longer term release of pST from alginate hydrogel samples was also observed over 4 weeks. The alginate hydrogel samples were prepared in accordance with Example 49. In these trials, after removal of the syneresis liquid the release media, i.e. PBS, was refreshed every 48 hours. Subsequent samples collected gave a progressive release profile. The results are shown in FIG. 9. FIG. 9A shows pST release on a weight basis while FIG. 9B shows release as a percentage of the initial pST loading. Linear release rates were observed during the initial 2 weeks, which then plateaued over the following 2 weeks.

Porous bulk alginate hydrogels prepared with PEG (35 kDa) as an added porogen (at concentrations of 0, 0.5, 1 or 2 wt % ratio) exhibited a modified longer term release rate. As a percentage of the initial loading after 2 weeks a total 29 to 44% of the pST is released.

Viscosity of Model Injectable Compositions

To investigate composition viscosity and injectability, model injectable compositions without biologically active agent were prepared. Model injectable compositions were prepared with three different component solutions, with each component solutions:

Part [A1]: 2% chitosan or 2% chitosan with 1 mg hydroxyapatite (HAp)/mL
Part [B1]: tripolyphosphate (TPP) solution (0.32M) or TPP solution (0.32M) with 1% chondroitin sulphate (ChS)
Part [C1]: Montanide ISA61 VG In these examples, 2 mL of [A1] (with or without HAp) was emulsified in 2 mL of [C1] then various volumes of [B1] (with or without ChS) were added dropwise under continuous shearing to produce microgel in emulsion formulation having the constituents [A1]: [B1]: [C1] in the following volumetric ratios: 2:2:0; 2:2:0.5; 2:2:1; 2:2:2; 2:2:3; 2:2:4 and 2:2:5. The emulsion flow behaviour and stability of the model injectable compositions was evaluated using stress rheology.

Figure 10:
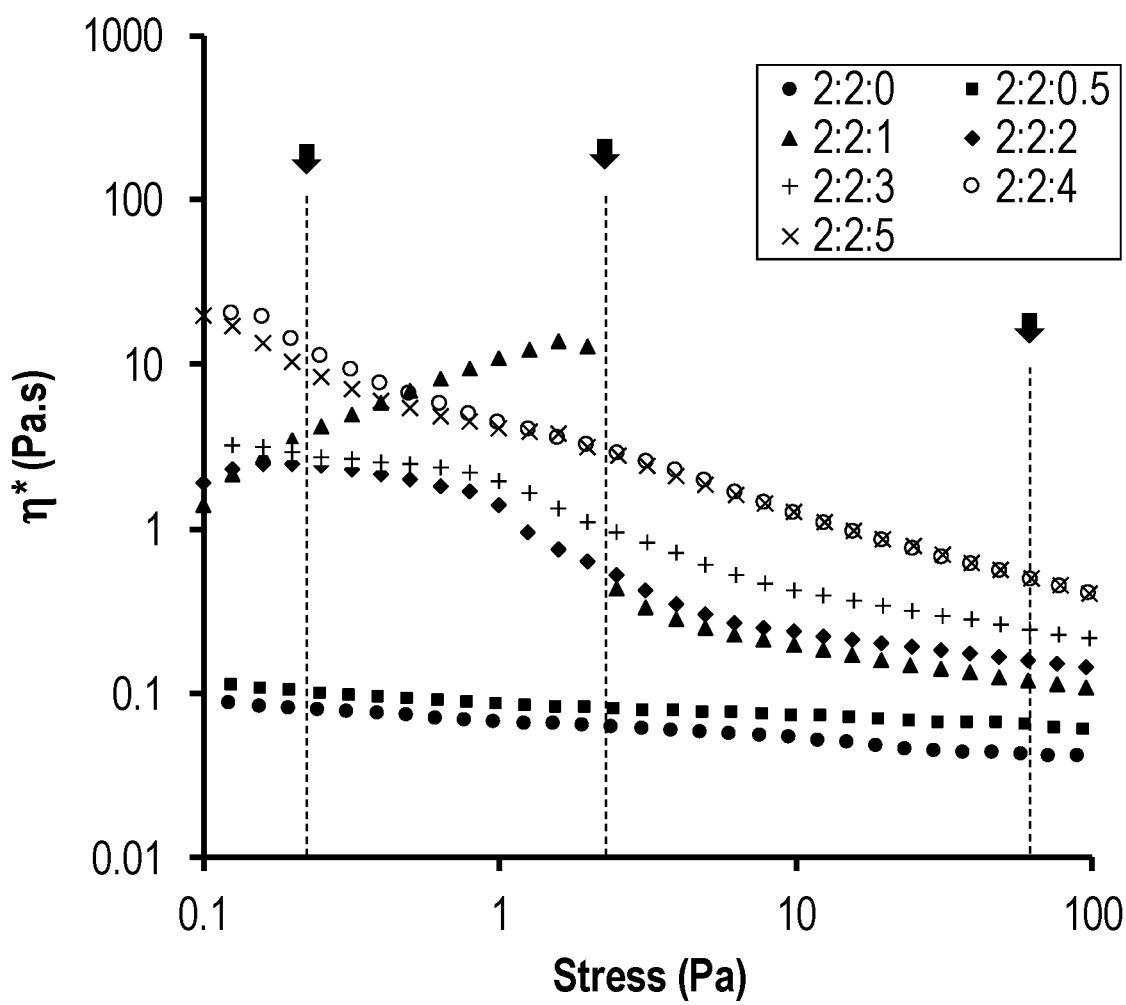
FIG. 10 is a graph showing changes in viscosity under applied shear stress for samples of injectable compositions of embodiments of the invention comprising crosslinked chitosan hydrogel particles with various crosslinking densities and aqueous phase volume ratio.

FIG. 10 gives the stress sweep measurements of the model injectable compositions where the volumetric ratios of the constituent components were varied between 2:2:0 to 2:2:5. As seen in FIG. 10, for injectable compositions formed with higher concentrations of the crosslinker TPP, viscosity can decrease with increasing shear stress due to shear thinning behaviour.

Figure 11:
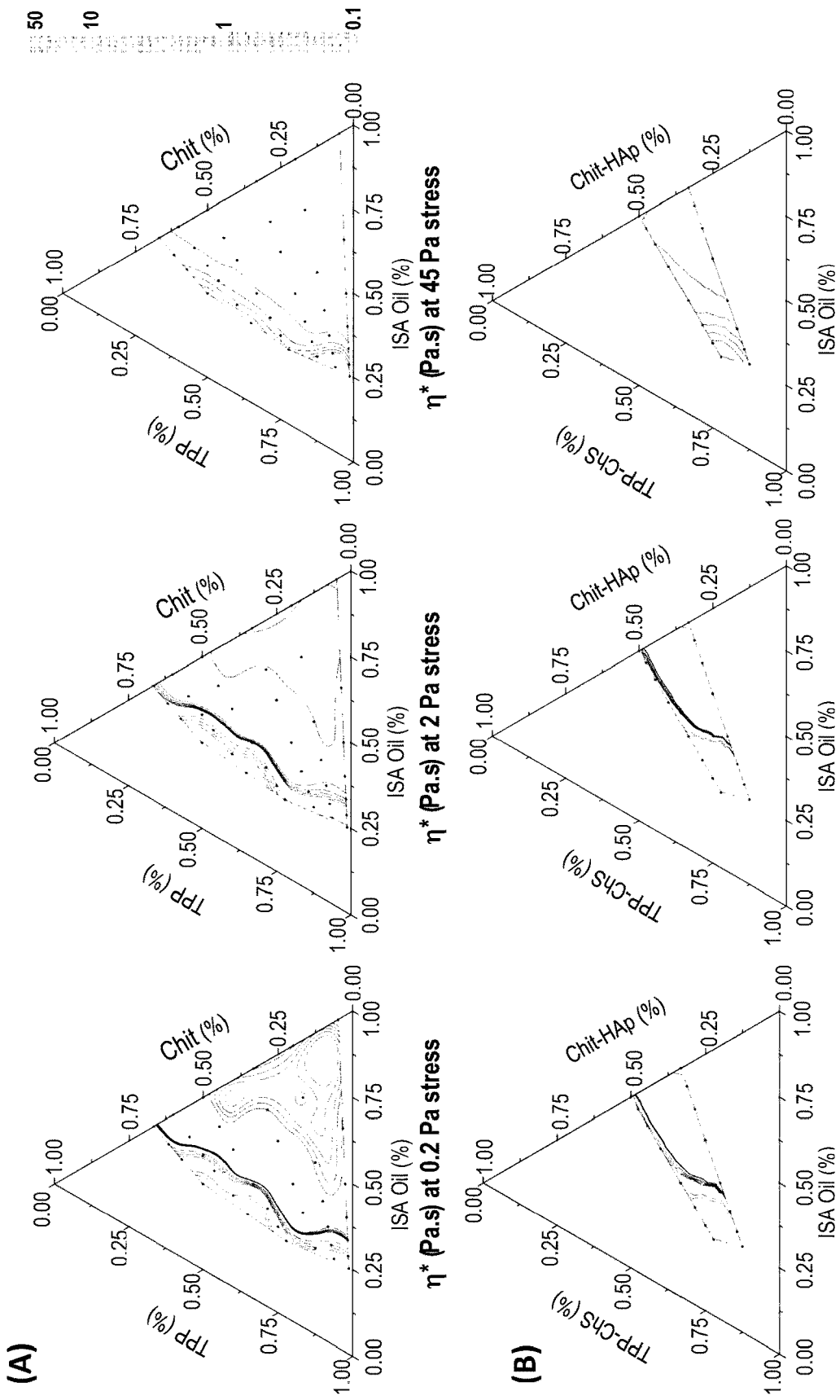
FIG. 11 shows compositional diagrams illustrating regions of low viscosity that correspond to the stresses indicated by the black arrows in FIG. 10 for (A) an injectable composition of one embodiment prepared with chitosan, TPP and montanide oil, and (B) an injectable composition of another embodiment prepared with chitosan/hydroxyapatite and TPP/chondroitin sulphate in montanide oil.

FIG. 11(A) gives the variation of flow viscosity for model injectable compositions formed using [A1] contains 2% chitosan and [B1] contains 0.32M TPP, where the volumetric ratios of [A1], [B1] and [C1] were varied to survey the overall stability of the model injectable composition and its flow behaviour, using viscosity θ* (Pa·s) as the control parameter. This variation in viscosity with composition is presented as ternary diagrams at three different shear stresses (0.2 Pa, 2 Pa and 45 Pa).

Flow viscosity measurements were also conducted on model injectable compositions formed using [A1] contains 2% chitosan with 1 mg/ml HAp and [B1] contains 0.32M TPP with 1% ChS, where the volumetric ratios of [A1], [B1] and [C1] compositions were varied. The results shown in FIG. 11(B) give corresponding flow behaviour, viscosity η* (Pa·s), of the different model injectable compositions at shear stresses of 0.2 Pa, 2 Pa and 45 Pa.

TSOL18 Antigen in Model Bulk Chitosan-Based Hydrogel

TSOL18 is anti-tapeworm antigen with positive charge (pI 9.65), contains 112 amino acids, with molecular mass of 12.8 kDa. In Examples 50 to 55, model bulk hydrogel particles containing TSOL18 were prepared. The hydrogels comprise TPP-crosslinked chitosan in their core. In some examples, other components, such as alginate, chondroitin sulphate and hydroxyapatite were also contained in the hydrogel, producing a composite hydrogel material.

Example 50

Model Bulk Chitosan-TPP Hydrogel with TSOL18

The following component solutions were prepared:
Part [M]: 2% chitosan in 1% AcOH
Part [N]: Tripolyphosphate (TPP) solution (0.08M)

In this example, TSOL18 was incorporated in component solution [M] at a concentration of 0.5 mg/mL. A quantity of [M] containing TSOL18 was then combined with an equal volume of [N] to form a TSOL18 loaded bulk chitosan hydrogel.

Example 51

Model Bulk Chitosan-TPP Hydrogel with TSOL18

The component solutions [M] and [N] of Example 50 were used in this example. However, TSOL18 was incorporated into component solution [N] instead at a concentration of 0.5 mg/mL. A quantity of [M] was combined with an equal volume of [N] containing TSOL18, to form a TSOL18 loaded bulk chitosan hydrogel.

Example 52

Model Bulk (Chitosan-HAp-TSOL18) Hydrogel and Chondroitin Sulphate Coating

The following component solutions were prepared:
Part [O]: 2% chitosan in 1% AcOH with 1 mg hydroxyapatite (HAp)/mL
Part [P]: Tripolyphosphate (TPP) solution (0.08M) with 1% chondroitin sulphate (ChS).

In this example, TSOL18 was incorporated in component solution [O] at a concentration of 0.5 mg/mL. A quantity of [O] containing TSOL18 was then combined with an equal volume of [P] to form a TSOL18 loaded bulk chitosan hydrogel core with a chondroitin sulphate (ChS) coating. The coating was non-crosslinked.

Example 53

Model Bulk (Chitosan-HAp) Hydrogel with Chondroitin Sulphate-TSOL18 Coating

The component solutions [O] and [P] of Example 52 were used in this example. However, TSOL18 was incorporated into component solution [P] at a concentration of 0.5 mg/mL instead. A quantity of [O] was combined an equal volume of [P] containing TSOL18, to form a bulk chitosan hydrogel with a non-crosslinked chondroitin sulphate (ChS) coating.

In this example, TSOL18 was incorporated in the ChS coating around the chitosan hydrogel core.

Example 54

Model Bulk (Chitosan-HAp-TSOL) Hydrogel with Alginate Coating

The following component solutions were prepared:
Part [O]: 2% chitosan in 1% AcOH with 1 mg hydroxyapatite (HAp)/mL
Part [Q]: tripolyphosphate (TPP) solution (0.08M) with 1% alginate.

In this example, TSOL18 was incorporated in component solution [O] at a concentration of 0.5 mg/mL. A quantity of [O] containing TSOL18 was then combined with an equal volume of [Q] to form a coated TSOL18 loaded bulk chitosan hydrogel. Here an alginate coating formed around the chitosan hydrogel loaded with TSOL18.

Example 55

Model Bulk (Chitosan-HAp) Hydrogel with Alginate-TSOL18 Coating

The component solutions [O] and [Q] of Example 54 were used in this example. However, TSOL18 was incorporated into component solution [Q] at a concentration of 0.5 mg/mL instead. A quantity of [O] was combined with an equal volume of [Q] containing TSOL18, to form a bulk chitosan hydrogel with an alginate coating. In this example, the TSOL18 was incorporated in the alginate coating around the chitosan hydrogel core.

Release of TSOL18 from Model Bulk Hydrogel

The initial syneresis release of TSOL18 (monitored over 1 week) from the bulk hydrogel samples prepared in Examples 50 to 55 is shown in FIG. 13. The following results can be seen in FIG. 13:

Example 50: The syneresis liquid contained 54% of the TSOL18 after 4 hours and remained the same after 24 hours. The release of TSOL18 increased to 78% after 1 week.

Example 51: The syneresis liquid contained 75% of the TSOL18 after 4 hours, which then reduced to 72% at 24 hours. The release of TSOL18 further decreased to 57% after 1 week.

Example 52: The syneresis liquid contained 44% of the TSOL18 after 4 hours and remained the same after 24 hours. The release of TSOL18 increased to 50% after 1 week, showing the effect of the chondroitin sulphate coating in modulating the release of TSOL18.

Example 53: The syneresis liquid contained 52% of the TSOL18 after 4 hours, which remained the same at 24 hours. The release of TSOL18 decreased to 45% after 1 week, showing the strong binding between TSOL18 and chondroitin sulphate in the coating.

Example 54: The initial syneresis release of TSOL18 from the bulk hydrogel (monitored over 1 week) is given in FIG. 13. As seen in FIG. 13, the syneresis liquid contained 34% of the TSOL18 after 4 hours, which increased to 49% after 24 hours. The release of TSOL18 reached an equilibrium at 66% after 1 week.

Example 55: The syneresis liquid contained 69% of the TSOL18 as measured after 4 hours, which then reduced to 66% after 24 hours and further reduced to 53% after 1 week. This shows that the initial interaction between TSOL18 and alginate enhances the incorporation of TSOL18 in the coating around the chitosan hydrogel.

Injectable Compositions Containing TSOL18 Antigen in Hydrogels with Chitosan Coating Injectable compositions containing chitosan coated hydrogels containing TSOL18 were prepared in accordance with Examples 56 to 59. The coated hydrogels were made by injecting ChS, alginate, ChS-TPP, or alginate-TPP constituent solutions into a chitosan-$CaCl_2$ constituent solution to form TSOL18 containing coated hydrogel particles having a chitosan coating as an outer layer. It is envisaged that the coated hydrogel could provide greater entrapment of TSOL18 and lower syneresis (i.e. lower free antigen in aqueous phase) due to the highly positively charged TSOL18 interacting electrostatically with negatively charged ChS or alginate in the hydrogel core.

Model Bulk Hydrogel with TSOL18 and Chitosan Coating

The following component solutions were prepared and used in the following examples 56 to 59:
Part [AC]: 1% $CaCl_2$ in 1% chitosan in 1% AcOH
Part [BT] 2% ChS with TSOL18 (0.5 mg/mL)
Part [CT] 2% ChS—0.01 M TPP with TSOL18 (0.5 mg/mL)
Part [DT] 2% alginate with TSOL18 (0.5 mg/mL)
Part [ET] 2% alginate—0.01 M TPP with TSOL18 (0.5 mg/mL)

In each of the Examples, component solutions [BT], [CT], [DT] or [ET] were injected into [AC] to form a hydrogel having a chitosan coating as a skin on the formed hydrogel. Calcium chloride was co-solubilized with the chitosan constituent to provide quick gel formation. The negatively charged cross-linker TPP can be included in the negatively charged ChS or alginate to help with formation of the chitosan coating and to increase its thickness if necessary.

Example 56

Bulk Chondroitin Sulphate Hydrogel with Chitosan Coating

A volume of [BT] was injected into an equal volume of [AC]. This produced a ChS—$Ca^{2+}$ hydrogel containing TSOL18 and with a chitosan coating. In this example, the chitosan coating is not crosslinked.

Example 57

Bulk Chondroitin Sulphate Hydrogel with Crosslinked Chitosan Coating

A volume of [CT] was injected into an equal volume of [AC]. This produced a ChS—$Ca^{2+}$ hydrogel containing TSOL18 and with a crosslinked chitosan coating, where the chitosan is crosslinked with TPP.

Example 58

Bulk Alginate-Ca Hydrogel with Chitosan Coating

A volume of [DT] was injected into an equal volume of [AC]. This produced an alginate-$Ca^{2+}$ hydrogel containing TSOL18 and with a chitosan coating. In this example, the chitosan coating is not crosslinked.

Example 59

Bulk Alginate-Ca Hydrogel with Crosslinked Chitosan Coating

A volume of [ET] was injected into an equal volume of [AC]. This produced an alginate-$Ca^{2+}$ hydrogel containing TSOL18 and with a crosslinked chitosan coating. In this example, TPP is used to form the crosslinked chitosan coating.

Syneresis Release of TSOL18 from Coated Bulk Hydrogel

The syneresis release of TSOL18 from the coated bulk hydrogel samples of Examples 56 to 59 into the aqueous liquid was measured after 4 and 24 hours. The results are shown in FIG. 14.

As seen in FIG. 14, the sample of Example 56 exhibited a constant syneresis release value of 24% of the initial amount of TSOL18 at 4 and 24 hours. Meanwhile, the syneresis release value of Example 57 was constant at 42% of the initial amount of TSOL18. This represents an increase in comparison to Example 56. It is thought that this increase could be due to an increase in the porosity of the chitosan-TPP coating allowing more of the TSOL18 to diffuse through to the aqueous liquid.

In Example 58, no TSOL18 syneresis into aqueous phase was observed after 4 and 24 hours. In comparison, in Example 59, TSOL18 syneresis release from this sample was increased compared to Example 58. A constant value of TSOL18 syneresis into the aqueous phase was measured after 4 and 24 hours at 6%. This increase may be due to an increase in the porosity of the chitosan-TPP coating. These examples also show that the interaction between TSOL18 and alginate is much stronger than the interaction between TSOL18 and chondroitin sulphate.

Example 60

Injectable Composition with Chitosan Coated Alginate Hydrogel Particles Containing TSOL18

The following component solutions were prepared and used:

Part [A3]: 2.8% CaCl2 in 2% chitosan in 1% AcOH

Part [D3] 2% alginate with TSOL18 (300 μg/mL)

Part [F1] Sesame oil with 20 mg Span 80/mL

A volume of [D3] containing TSOL18 was emulsified in [F] using high shear emulsifier. To this primary emulsion a volume of [A3] was added drop wise under constant shear. The ratio of the component solutions [F1]:[D3]:[A3] was 2:1:0.5. The resulting composition is shown in FIG. 16.

Injectable Composition with TSOL18 Anti-Tapeworm Vaccine

The following component solutions were used to prepare various injectable compositions containing TSOL18 loaded hydrogels:

Part [M]: 2% chitosan in 1% AcOH

Part [N]: Tripolyphosphate (TPP) solution (0.08M)

Part [O]: 2% chitosan in 1% AcOH with 1 mg hydroxyapatite (HAp)/mL

Part [P]: Tripolyphosphate (TPP) solution (0.08M) with 1% chondroitin sulphate (ChS).

Part [Q]: Tripolyphosphate (TPP) solution (0.08M) with 1% alginate.

Example 61

Injectable Composition Comprising Chitosan-TPP Hydrogel with TSOL18

In this example, TSOL18 was incorporated in component solution [M] at a concentration of 0.5 mg/mL A volume of [M] containing TSOL18 (0.25 mL) was emulsified in 1 mL of Montanide ISA 61 VG oil using high shear emulsifier. To this primary emulsion 0.25 mL of [N] was added drop wise under constant shear. The resulting composition was a stable uniform emulsion with below 1 μm droplet diameter.

Example 62

Injectable Composition Comprising Chitosan-TPP Hydrogel with TSOL18

TSOL18 was incorporated in component solution [N] at a concentration of 0.5 mg/mL. A volume of [M] (0.25 mL) was emulsified in 1 mL of Montanide ISA 61 VG oil using high shear emulsifier. To this primary emulsion 0.25 mL of [N] containing TSOL18 was added drop wise under constant shear. The resulting composition was a stable uniform emulsion with below 1 μm droplet diameter. An example is shown in FIG. 15.

Example 63

Injectable Composition Comprising (Chitosan-HAp)-(ChS-TPP) Hydrogel with TSOL18

TSOL18 was incorporated in component solution [O] at a concentration of 0.5 mg/mL. A volume of [O] containing TSOL18 (0.25 mL) was emulsified in 1 mL of Montanide ISA 61 VG oil using high shear emulsifier. To this primary emulsion 0.25 mL of [P] was added drop wise under constant shear. The resulting injectable composition was a stable uniform emulsion with below 1 μm droplet diameter. The hydrogel particles in the composition comprise a crosslinked chitosan-HAp core and a coating comprising chondroitin sulphate.

Example 64

Injectable Composition Comprising (Chitosan-HAp)-(ChS-TPP) Hydrogel with TSOL18

The component solutions [O] and [P] of Example 62 were used in this example. However, TSOL18 was incorporated into component solution [P] at a concentration of 0.5 mg/mL instead. A volume of [O] containing TSOL18 (0.25 mL) was emulsified in 1 mL of Montanide ISA 61 VG oil using high shear emulsifier. To this primary emulsion 0.25 mL of [P] was added drop wise under constant shear. The resulting injectable composition was a stable uniform emulsion with below 1 μm droplet diameter. The hydrogel particles in the composition comprise a crosslinked chitosan-HAp core and a coating comprising chondroitin sulphate.

Example 65

Injectable Composition Comprising (Chitosan-HAp)-(Alginate-TPP) Hydrogel with TSOL18

TSOL18 was incorporated in component solution [O] at a concentration of 0.5 mg/mL. A volume of [O] containing TSOL18 (0.25 mL) was emulsified in 1 mL of Montanide ISA 61 VG oil using high shear emulsifier. To this primary emulsion 0.25 mL of [Q] was added drop wise under constant shear. The resulting injectable composition was a stable uniform emulsion with below 1 μm droplet diameter. The hydrogel particles in the composition comprise a crosslinked chitosan-HAp core and coating comprising alginate.

Example 66

Injectable Composition Comprising (Chitosan-HAp)-(Alginate-TPP) Hydrogel with TSOL18

The component solutions [O] and [Q] of Example 64 were used in this example. However, TSOL18 was incorporated into component solution [Q] at a concentration of 0.5 mg/mL instead. 0.25 mL of [O] was emulsified in 1 mL of Montanide ISA 61 VG oil using high shear emulsifier. To this primary emulsion 0.25 mL of [Q] was added drop wise under constant shear. The resulting injectable composition was a stable uniform emulsion with below 1 µm droplet diameter. The hydrogel particles in the composition comprise a crosslinked chitosan-Hap core and a coating comprising alginate.

Injectable Composition Containing Chitosan Coated Hydrogel Particles and TSOL18 Anti-Tapeworm Vaccine The following component solutions were used to prepare various injectable compositions containing TSOL18 loaded coated hydrogels:

Part [AC]: 1% $CaCl_2$ in 1% chitosan in 1% AcOH
Part [BT] 2% ChS with TSOL18 (0.5 mg/mL)
Part [CT] 2% ChS—0.01 M TPP with TSOL18 (0.5 mg/mL)
Part [DT] 2% alginate with TSOL18 (0.5 mg/mL)
Part [ET] 2% alginate—0.01 M TPP with TSOL18 (0.5 mg/mL)

Example 67

Injectable Composition Comprising Chitosan Coated Chondroitin Sulphate Hydrogel with TSOL18

A volume of [BT] was emulsified in 1 mL of Montanide ISA 61 VG oil using high shear emulsifier. To this primary emulsion 0.25 mL of [AC] was added drop wise under constant shear. The resulting composition was a stable uniform emulsion with below 1 µm droplet diameter. This produced an injectable composition having ChS—$Ca^{2+}$ hydrogel particles containing TSOL18 and with a chitosan coating.

Example 68

Injectable Composition Comprising Crosslinked Chitosan Coated Chondroitin Sulphate Hydrogel with TSOL18

A volume of [CT] was emulsified in 1 mL of Montanide ISA 61 VG oil using high shear emulsifier. To this primary emulsion 0.25 mL of [AC] was added drop wise under constant shear. The resulting composition was a stable uniform emulsion with below 1 µm droplet diameter. This produced an injectable composition having ChS—$Ca^{2+}$ hydrogel particles containing TSOL18 and with a crosslinked chitosan-TPP coating.

Example 69

Injectable Composition Comprising Chitosan Coated Alginate Hydrogel with TSOL18

A volume of [DT] was emulsified in 1 mL of Montanide ISA 61 VG oil using high shear emulsifier. To this primary emulsion 0.25 mL of [AC] was added drop wise under constant shear. The resulting composition was a stable uniform emulsion with below 1 µm droplet diameter. This produced an injectable composition having alginate-$Ca^{2+}$ hydrogel particles containing TSOL18 and with a non-crosslinked chitosan coating.

Example 70

Injectable Composition Comprising Crosslinked Chitosan Coated Alginate Hydrogel with TSOL18

A volume of [ET] was emulsified in 1 mL of Montanide ISA 61 VG oil using high shear emulsifier. To this primary emulsion 0.25 mL of [AC] was added drop wise under constant shear. The resulting composition was a stable uniform emulsion with below 1 µm droplet diameter. This produced an injectable composition having alginate-$Ca^{2+}$ hydrogel particles containing TSOL18 and with a crosslinked chitosan-TPP coating.

It is to be understood that various other modifications and/or alterations may be made without departing from the spirit of the present invention as outlined herein.

The invention claimed is:

1. An injectable composition for rapid and sustained delivery of a biologically active agent comprising:
    a water-in-oil emulsion comprising an aqueous phase dispersed in an oil phase, the aqueous phase comprising a plurality of hydrogel particles and an aqueous liquid; and
    a biologically active agent in the hydrogel particles and in the aqueous liquid of the aqueous phase,
    wherein the biologically active agent is selected from the group consisting of hormones, antimicrobial agents, therapeutic antibodies, cytokines, fusion proteins, viruses, bacteria and bacteria fragments, antigens, and combinations of any two or more thereof;
    wherein the hydrogel particles comprise a crosslinked polysaccharide selected from chitosan crosslinked with a phosphate compound and alginate crosslinked with a divalent cation derived from an alkaline earth metal;
    wherein said composition exhibits shear thinning when injected through a lumen of a needle; and
    wherein, when administered, the injectable composition provides rapid and sustained delivery of the biologically active agent in vivo.

2. The composition according to claim 1, wherein the composition further comprises an adjuvant.

3. The composition according to claim 2, wherein the oil phase of the emulsion comprises the adjuvant.

4. The composition according to claim 2, wherein the oil phase of the emulsion comprises an adjuvanting oil.

5. The composition according to claim 1, wherein the crosslinked polysaccharide comprises chitosan crosslinked with tripolyphosphate.

6. The composition according to claim 1, wherein the hydrogel particles further comprise chondroitin sulphate or chondroitin sulphate which is crosslinked with a divalent cation derived from an alkaline earth metal.

7. The composition according to claim 1, wherein the hydrogel particles have an average particle diameter in the range of from about 10 nm to 20 µm when measured by dynamic light scattering, light microscopy, or confocal laser scanning microscopy.

8. The composition according to claim 1, wherein the hydrogel particles further comprise an aqueous insoluble alkaline earth metal phosphate.

9. The composition according to claim 1, wherein one or more of the plurality of hydrogel particles comprise a coating.

10. The composition according to claim 1, wherein the water-in-oil emulsion comprises a surfactant.

11. The composition according to claim 1, wherein the biologically active agent is selected from the group consisting of antigens, hormones, and combinations of any two or more thereof.

12. The composition according to claim 1, wherein the biologically active agent in the hydrogel particles is conjugated to the particles.

13. A method of delivering a biologically active agent to a subject, comprising administering the composition of claim 1 to the subject by injection.

14. A method of treating a disease or disorder in a subject, comprising administering the composition of claim 1 to the subject by injection.

15. The method according to claim 14, wherein the disease or disorder is a microorganism infection or a viral infection.

16. A process for preparing the composition of claim 1, comprising:
   providing a first aqueous composition comprising a first hydrogel-forming component and a second aqueous composition comprising a second hydrogel-forming component, at least one of the first aqueous composition and the second aqueous composition comprising a biologically active agent;
   combining the first aqueous composition with a lipophilic composition comprising an oil to form an emulsified composition; and
   combining the second aqueous composition with the emulsified composition under conditions allowing the first hydrogel-forming component to react with the second hydrogel-forming component to form a plurality of hydrogel particles in situ and thereby provide an injectable composition comprising a water-in-oil emulsion comprising an aqueous phase dispersed in an oil phase, the aqueous phase comprising a plurality of hydrogel particles and an aqueous liquid, wherein the biologically active agent is contained in the hydrogel particles and in the aqueous liquid of the aqueous phase of the water-in-oil emulsion.

17. The composition according to claim 8, wherein the aqueous insoluble alkaline earth metal phosphate is hydroxyapatite.

18. The composition according to claim 1, wherein the hydrogel particles further comprise chondroitin sulphate or chondroitin sulphate which is crosslinked with a divalent cation derived from an alkaline earth metal, and further comprise an aqueous insoluble alkaline earth metal phosphate.

19. The composition according to claim 1, wherein the hydrogel particles further comprise chondroitin sulphate or chondroitin sulphate which is crosslinked with a divalent cation derived from an alkaline earth metal, and further comprise an aqueous insoluble alkaline earth metal phosphate which is hydroxyapatite.

20. The composition according to claim 10, wherein the surfactant comprises a nonionic surfactant selected from the group consisting of glycols, glycerol esters, polyoxyethylene/propylene glycols, polysorbates, sorbitan monooleate, sorbitan monolaurate, sorbitan monopalmitate, sesquioleate, trioleate, tristearate, saccharides, and polysaccharides.

21. The composition according to claim 1, wherein the hydrogel particles comprise a chitosan crosslinked with a tripolyphosphate, chondroitin sulphate, and hydroxyapatite.

22. The composition according to claim 1, wherein the biologically active agent is selected from Bm86 antigen, somatotropin, and TSOL18 antigen.

23. The composition according to claim 1, wherein the composition is a vaccine composition.

24. The process according to claim 16, wherein the first hydrogel-forming component comprises chitosan or, chitosan and hydroxyapatite.

25. The process according to claim 16, wherein the second hydrogel-forming component comprises a tripolyphosphate and chondroitin sulphate.

26. The process according to claim 16, wherein the first hydrogel-forming component comprises chitosan or, chitosan and hydroxyapatite, and the second hydrogel-forming component comprises a tripolyphosphate and chondroitin sulphate.

* * * * *